United States Patent [19]
Lakowicz et al.

[11] Patent Number: 5,485,530
[45] Date of Patent: Jan. 16, 1996

[54] METHOD AND APPARATUS FOR MULTI-DIMENSIONAL PHASE FLUORESCENCE LIFETIME IMAGING

[75] Inventors: Joseph R. Lakowicz, 9142 Emersons Reach, Columbia, Md. 21045; Klaus W. Berndt, Baltimore; Kazimierz Nowaczyk, Baltimore; Henryk Szmacinski, Baltimore, all of Md.; Michael L. Johnson, Charlottesville, Va.

[73] Assignee: Joseph R. Lakowicz, Columbia, Md.

[21] Appl. No.: 94,016

[22] PCT Filed: Jul. 23, 1993

[86] PCT No.: PCT/US92/00242

§ 371 Date: Jul. 23, 1993

§ 102(e) Date: Jul. 23, 1993

[87] PCT Pub. No.: WO92/13265

PCT Pub. Date: Aug. 6, 1992

Related U.S. Application Data

[63] Continuation-in-part of Ser. No. 645,525, Jan. 24, 1991, abandoned.

[51] Int. Cl.[6] ..................................................... G06K 9/00
[52] U.S. Cl. ........................ 382/191; 382/133; 250/459.1
[58] Field of Search ........................... 382/6, 58, 191, 382/128, 133, 312, 129; 250/461.2, 458.1, 459.1; 356/73, 317, 318, 417, 346

[56] References Cited

U.S. PATENT DOCUMENTS

| | | | |
|---|---|---|---|
| 4,791,310 | 12/1988 | Honig et al. | 250/458.1 |
| 5,093,866 | 3/1992 | Douglas-Hamilton | 382/6 |
| 5,159,397 | 10/1992 | Kosaica | 356/73 |

OTHER PUBLICATIONS

Gratton et al. "Parallel Acquisition of Fluoresence Decay Using Array Detector", Proceedings of the SPIE, vol. 1204, 1, Oct. 1990, pp. 21–23.

McGown et al. "Phase Resolved Luminesence Spectroscopy", Analytical Chemistry, vol. 56, No. 13, 1, Nov. 1984, pp. 1400A–1402A.

*Primary Examiner*—Yon J. Couso
*Attorney, Agent, or Firm*—Rothwell, Figg, Ernst & Kurz

[57] ABSTRACT

A method and apparatus for detection and/or measurement of physical characteristics of a sample based on multi-dimensional phase-modulation fluorescence lifetime imaging using at least one fluorescent probe having known and/or variable fluorescent lifetimes.

2 Claims, 23 Drawing Sheets

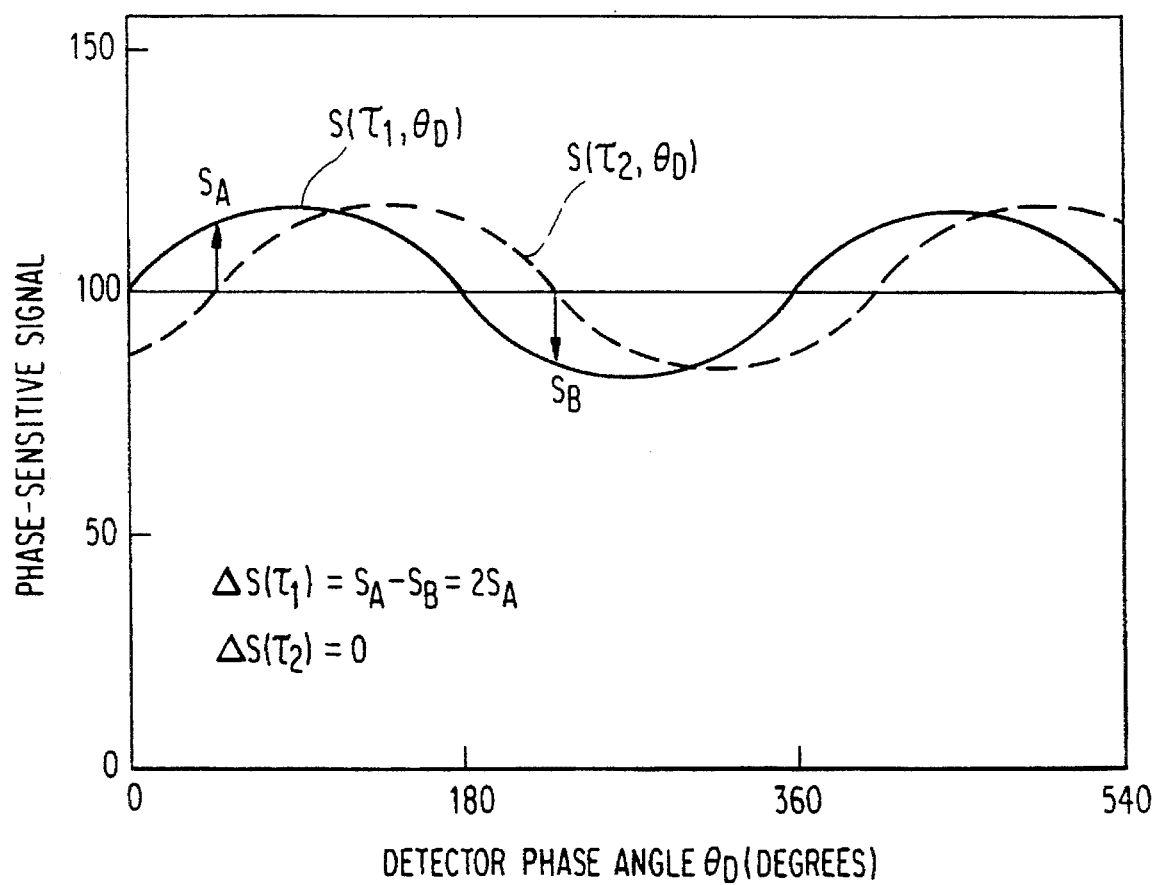

RHODAMINE 6G
AND
RHODAMINE B

RHODAMINE B
SUPPRESSED

RHODAMINE 6G
SUPPRESSED

REGULAR IMAGE

BACKGROUND SUPPRESSED

PLATEAU SUPPRESSED

FLUORESCENCE STANDARDS

PHASE IMAGING AT $f_{MOD} = 37.999$ MHz

SCATTERER    POPOP    PERYLENE    3-AFL

FLUORESCENCE STANDARDS
MODULATION LIFETIME IMAGING

FLUORESCENCE STANDARDS
PHASE LIFETIME IMAGING

SCATTERER   POPOP   PERYLENE   3-AFL

FLUORESCENCE STANDARDS
MODULATION IMAGING AT $f_{MOD} = 37.999$ MHz

SCATTERER    POPOP    PERYLENE    3-AFL

RHODAMINE 6G QUENCHED BY POTASSIUM IODIDE
PHASE AND MODULATION IMAGING AT $f_{MOD}=76.2$ MHz

RHODAMINE 6G QUENCHED BY POTASSIUM IODIDE
LIFETIME IMAGING

SCATTERER  0    0.03   0.1 M IODIDE 1,2-BENZANTHRACENE QUENCHED BY OXYGEN
PHASE AND MODULATION IMAGING AT $f_{MOD}=18.9995$ MHz

+O₂   AIR   +ARGON   POPOP

NADH
FIG.23(A) PHASE, MODULATION AND LIFETIME IMAGING AT $f_{MOD}$=75.998 MHz
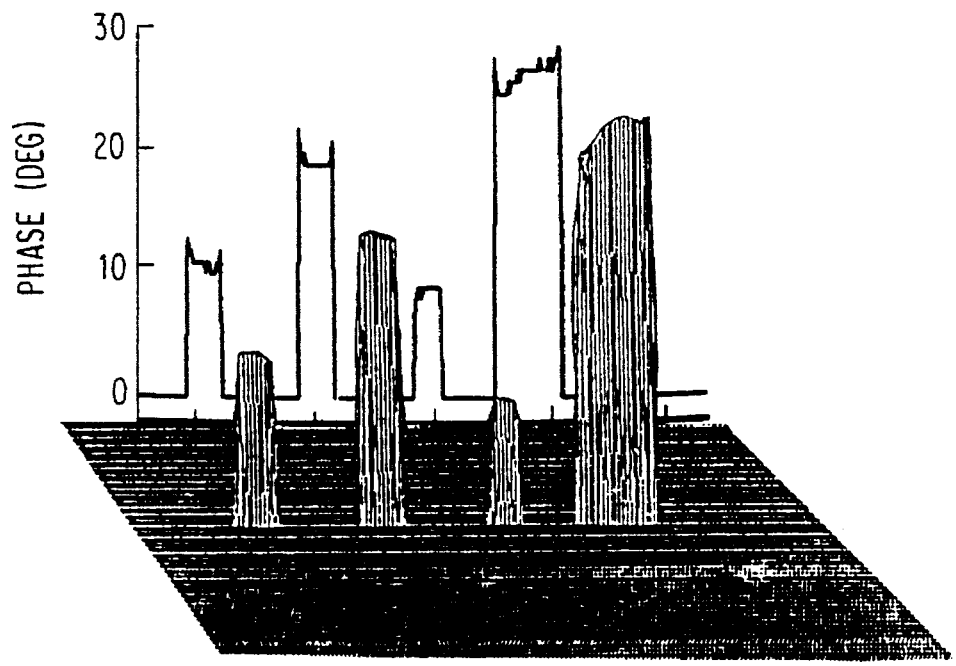
FIG.23(B)
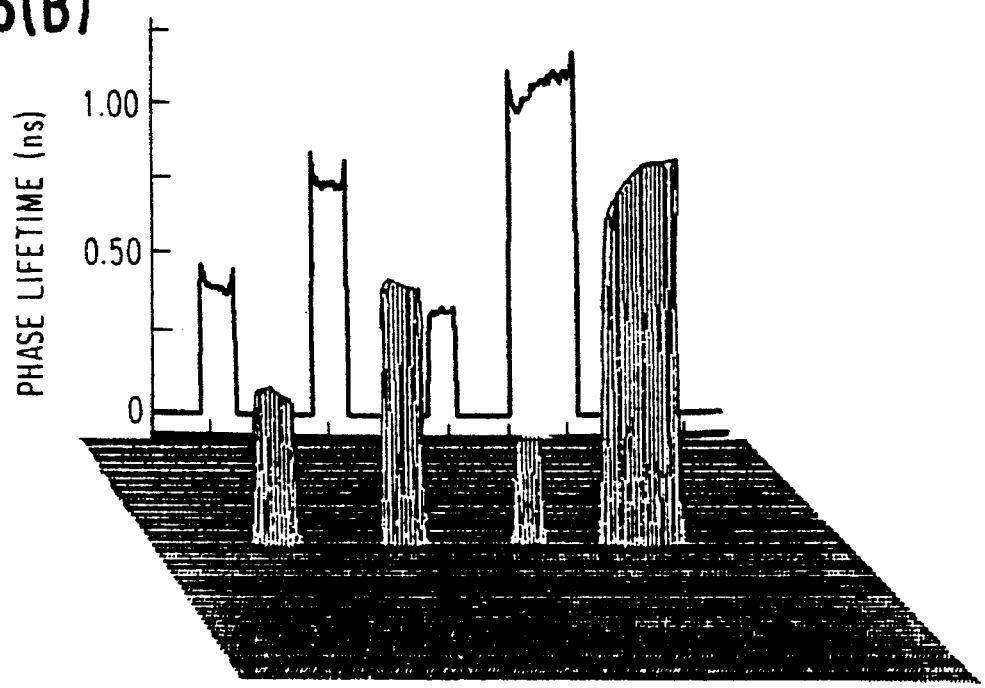

METHOD AND APPARATUS FOR MULTI-DIMENSIONAL PHASE FLUORESCENCE LIFETIME IMAGING

This application is a 371 of PCT/US92/00242 filed Jul. 23, 1993 and a Continuation-in-part of patent application Ser. No. 07/645,525 filed Jan. 24, 1991 which is now abandoned.

BACKGROUND OF THE INVENTION

1. Field of the Invention

The present invention generally relates to a method and apparatus for providing fluorescence lifetime images and more particularly to a method and apparatus for providing multi-dimensional fluorescence lifetime imaging, using the phase-shift and/or modulation of the fluorescence signal. Also described is a method to suppress the fluorescence signal due to background and/or autofluorescence from the sample, or to visualize regions of the sample with decay times greater or less than a desired value.

2. Description of the Background Art

Quantitative fluorescence image analysis has application to a wide variety of practical arts including cellular physiology and biological and clinical research, immunology, chromosome analysis, environmental science, forensic analysis, fingerprint imaging and the like. However, significant problems have been encountered in such applications.

The availability of a variety of quantitative techniques for the evaluation of the chemical composition of specimens is of significant importance to the conduct of basic biological research and to a wide variety of clinical applications. Research involving the study and analysis of cells, generally known as cytology, employs a variety of analytical techniques for identifying and enumerating the subpopulations of cells in a specimen under study. For example, cytological materials may be examined to detect the presence of cancerous or malignant cells, or to determine the chemical composition of cells within a specimen. For purposes of analysis, the cells may be labeled with a variety of fluorescent materials, commonly known as probes or fluorophores, which have an identified affinity for cells or cell components which are of interest to an analysis. The probes will emit a particular fluorescence when stimulated by light at a known wavelength. The emitted light may have distinguishing characteristics, particularly wavelength and intensity, which permit an analysis of a subpopulation of cells or region of a cell to be conducted. The wavelength and intensity are dependent on the concentration of the analyte or cell component but, due to background or autofluorescence, measurements based on intensity or wavelength are limited to detection of analytes or compounds that are present at the highest concentrations in a cell or sample.

The study of collections of multiple cells using fluorescence spectroscopy has obvious additional problems such that an accurate determination of the number of cells in a subpopulation which have a given characteristic usually cannot be made since it is difficult to separate the subpopulations for analysis.

In one conventional approach using fluorescence microscopy (FM), specimens are tagged with fluorescent agents which bind or react with particular components of a specimen or cell component, and which are responsive to light emitted by a non-modulated light source at a characteristic wavelength to which the agent is sensitive.

When the fluorescent agent, bound to or reacted with a specimen, is excited by light at the agent's absorption wavelength, the energy level of an electron of the agent is raised above the relaxed or ground state to an excited state. Following excitation, the agent's electrons return to their relaxed state and emit light having a characteristic wavelength. Multiple agents may be used, each sensitive to light at the same or different wavelengths and each responsive to the stimulating light by emitting light at a characteristic wavelength that can be detected and used for analysis. Each agent can be responsive to various chemicals or biological molecules within the cell.

In a conventional FM system, as a particular fluorophore emits light following its excitation, a two-dimensional intensity image may be produced that is proportional to the local concentration of the fluorescent species having the characteristic wavelength which is detected. The areas having the highest intensity light emissions are detectable and identifiable as areas having the highest concentration of the related probe. The areas of less concentration of analyte, however, are not detectable, due to, e.g., high background fluorescence or autofluorescence. However, the concentration of the probe is often not of interest, but, rather, the important parameters include the concentration of an analyte to which the probe is responsive.

Thus, one major problem of such conventional two-dimensional fluorescence intensity imaging methods is that the measurement is concentration-dependent and often is not of interest or may be inaccurate due to the difficulty with fluorophore bleaching (i.e., a degradation of the fluorophore caused by the intensity of the incident laser light). The limitation of concentration-dependent measurements and the problem of photobleaching preclude accurate characterization of the chemical and physical properties of a specimen by conventional FM techniques. Additional limitations include the above-mentioned background and autofluorescence, as described in greater detail below.

The problem of photobleaching and the effects of probe concentration-dependent intensities are sometimes circumvented using probes which display wavelength shifts in response to the chemical species of interest. These probes were developed because conventional FM measurements are performed only as stationary measurements, and wavelength shifts are needed to cancel concentration and photobleaching effects. Additionally, few such wavelength-ratio probes are available, and these require excitation with ultraviolet light which causes problems including increased autofluorescence, cost and complexity, due to the general unavailability of ultraviolet lasers. These significant technical problems arise due to the need for a probe to display a special shift in order to eliminate concentration effects.

As seen in U.S. Pat. No. 4,778,539, Yamashita et al, issued Oct. 18, 1988, individual cells may be distinguished by measuring light at an observation point of a flow cytometer system. There, the change in the intensity of transient emitted light over a period of time, following excitation by short pulses of laser light, may be measured and used to detect the attenuation time of the emitted light, the rise time of the emitted light and the orientation relaxation time. These parameters may be used as a basis for cell discrimination. However, such measurements are performed cell-by-cell, and do not allow for rapid and/or simultaneous scanning of a population of cells, and do not allow for distinguishing regions within a cell.

There have been some attempts to measure lifetimes using a microscope and laser to provide site-selective measurements. See, for example, Fernandez *Biophys. J.*, 37:73a (1982); Ramponi and Rodgers *Photochem. and Photobiol.*, 45:161–165 (1987); Docchio et al *J. Microscopy*, 134:151–160 (1983); and Keating and Wensel *SPIE*, 1204:42–48 (1990). However, such measurements are complex even when performed at a single site, and these methods are not easily extended to two dimensional imaging. For instance, the technique of photon-counting lifetime measurements by timeresolved fluorescence through a microscope has been extended by scanning single pixels by Wang et al (*Applied Spectroscopy*, 44:25–30 (1990)) to provide two-dimensional mapping of samples. However, these images are limited to the use of spot-by-spot, or pixel-by-pixel, measurements under the microscope.

Phase-modulation fluorescence spectroscopy (PMFS) provides further means by which fluorescence lifetime selectivity can be implemented in a static environment. See J. R. Lakowicz, *Principles of Fluorescence Spectroscopy*, Plenum Press (1983), which teaches a technique in which a sample is excited with light having a periodic time-dependent intensity, and detection is made of the resulting time-dependent emission. Because the emission is demodulated and phase shifted to an extent determined by the fluorescence lifetime of the species, the fluorescence lifetime ($\tau$) can be calculated from the phase shift of the species:

$$\tau = \frac{1}{\omega} \tan \phi$$

or from a demodulation factor $$\tau = \frac{1}{\omega} \left[ \frac{1}{m^2} - 1 \right]^{1/2}$$

where m is a demodulation factor, $\omega$ is the angular modulation frequency and $\phi$ is the phase shift of the species. A modification of PMFS is the technique of phase-sensitive detection or phase-resolved fluorescence spectroscopy (PRFS), which results from a comparison of the detected emission with an internal electronic reference signal of the same frequency. phase-sensitive detection can be accomplished by using the high light- modulation frequencies (see, e.g., Veselova et al *Opt. Spect.*, 29:617–618 (1970) and Veselova and Shirokov *Akad. Nauk. SSSR Bull. Phys. Sci.* 36:925–928 (1972)) and more easily at lower cross-correlation frequencies. See Lakowicz and Cherek *J. Biochemo Biophys. Methods*, 5:19–35 (1981).

In phase-resolved fluorometry, the time-dependent fluorescence photocurrent is multiplied by a periodic square-wave signal which has the same modulation frequency as the fluorescence signal, in order to fully detect an output signal, and is then integrated. A time-independent DC signal is thereby produced that is proportional to the cosine of the difference between the phase angles of the square wave and the fluorescence signal, and proportional to both signal amplitudes. However, it is important to recognize that the output signal in phase-resolved fluorescence is still proportional to the signal intensity.

The use of phase-resolved methods has been suggested for obtaining a scanning measurement of single pixels to generate a two-dimensional fluorescent measurement. For instance, Wang et al (*Applied Spectroscopy*, 43:840–845 (1989)) suggested a fluorescence lifetime distribution measurement system using an image dissector tube with phase-resolved detection. However, such methods suffer from the problem that measurements can be obtained only at a single spot or pixel, and the image is constructed by scanning of the spot.

A further problem of such scanning fluorescence measurements is that background and/or autofluorescence can each contribute to poor image contrast, particularly where the intensity level of fluorescent signals is low or the contrast between different fluorescent signals is small.

Attempts have been made to practically detect and diagnose early stage cancer by hematoporphyrin derivative (HpD) fluorescence analysis. HpD is an effective photosynthesizer in photodynamic therapy for treatment of a variety of solid malignant tumors in man. Picosecond fluorescence spectroscopy, however, has shown that the major detectable HpD fluorescence originates from monomers that show no tumor localizing ability. In contrast, the HpD which accumulates in cancerous tissue exists primarily as aggregates which are only weakly fluorescent. Hence, even though HpD aggregates accumulate preferentially in cancerous tissue, the relative increase in intensity is modest, due to the influence of background and auto fluorescence. Thus, such a method of quantitative image analysis suffers from a low contrast of fluorescence from cancer cells as compared to that from normal cells.

In an attempt to overcome such problems, blue-violet alternating-wavelength fluorescence excitation may be used to increase the contrast. However, such a corresponding system is very complex and has limited practical applicability. The ability to obtain image contrast based on lifetimes rather than intensity may allow superior localization of cancerous tissues.

Background and auto-fluorescence also present a problem when latent fingerprints are detected by laser-excited fluorescence using techniques that are now employed by law enforcement agencies world-wide. Such techniques for the detection of fingerprints via the inherent fingerprint fluorescence suffer from the problem that suitable detection is possible only on surfaces that display little or no background fluorescence. However, most surfaces of practical interest show intensive autofluorescence which can make direct fingerprint detection impractical or impossible.

Fingerprint and other fluorescence imaging techniques can achieve autofluorescence signal suppression, or superior contrast between regions of interest, by utilizing time-resolved imaging. For example, because many autofluorescent surfaces of practical interest display fluorescence lifetimes as short as 0.1 ns to about 2 ns, fingerprints may be treated with staining dyes that have extremely long fluorescent lifetimes, typically 1 $\mu$s or longer. By applying square wave-modulated laser excitation, the fast-decaying autofluorescence signal can be suppressed by means of an image intensifier with delayed ON-gating. However, the technique of pulsed image intensifier gating is restricted to fluorescence lifetimes that differ by at least ten-fold, in order to allow for an efficient lifetime-based selective signal suppression. For lifetimes that differ by less than ten-fold, e.g., by a factor of two, no significant contrast enhancement can be expected.

Moreover, only the signal corresponding to the component with the shorter lifetime can be suppressed entirely. The signals of the component having the longer lifetime can be suppressed only in part because they are time-overlapping with the fast-decaying signal.

In general, however, optional and complete suppression of either the fast-decaying or the slow-decaying signal is of interest to distinguish between lifetimes of similar values. For instance, in the case of a HpD-based method of cancer detection, the HpD aggregates accumulating in cancerous cells exhibit a lifetime of 0.1 ns, and monomers that show no tumor localizing ability have a longer decay time close to 4 ns. In this case, one would be interested in suppressing the signal of the 4-ns component. However, efficient suppression of the long decay time component based on pulse-gating is not readily realized, because commercially available image intensifiers allow only for a minimum gating time of about 5 ns. Due to the rise and fall time of the gating characteristic, no efficient time-selective signal suppression can be expected if both fluorophores have lifetimes shorter than 5 ns. Hence, it is desirable to be able to selectively observe the long or short decay time components in the emission.

A sinusoidally modulated image intensifier, combined with a linear photodiode array, has been utilized to acquire time-resolved fluorescence spectral data, as reported by Gratton et al (*SPIE*, 1204:21 (1990), but this apparatus was not used for position-sensitive measurements or to create lifetime images. Also, radio-frequency phase-sensitive imaging has been performed by using a position-sensitive high-speed photodetector, combined with an electronic correlator. See *SPIE*, 1204:798 (1990).

A conventional image intensifier pulse-gating technique for time-resolved imaging is illustrated schematically in FIG. 1. The fluorescent target 1 under test is illuminated by ultrashort periodic laser pulses 2. Two small areas 3, 4, one with a long decay time $\tau_2$ and one with a short decay time $\tau_1$, are shown on the target. By applying properly delayed electrical square wave pulses 5 to the image intensifier 6, imaging of the fast-decaying fluorescent area 4 onto the phosphor screen 7 can be suppressed, yielding only an image 3'.

As discussed above, no efficient decay time-selective suppression is possible if both decay times are comparable, or if both are too short. Also, only incomplete imaging suppression is attainable for the area 3 showing a longer decay time, due to time-overlapping with the emission emerging from the area 4 with the shorter decay time. The decay time, when compared to the square wave pulse 5 input to the image intensifier, is illustrated in FIG. 1 for each of the long decay time 8 and short decay time 9.

SUMMARY OF THE INVENTION

In view of the above identified problems with conventional techniques, it is an object of the present invention to provide a method and apparatus for obtaining multi-dimensional phase and/or modulation fluorescence lifetime imaging.

Another object of the present invention is to provide such a method and apparatus for detection and/or measurement of physical characteristics of a specimen, such as fluorescence microscopy, chromosome analysis, fingerprint detection and remote temperature imaging. In microscopy, such imaging of the present invention can provide chemical or physical images based on cation concentrations, anion concentrations, oxygen, pH and viscosity, for example.

It is also an object of the present invention to provide the above methods and apparatus based on the time-resolved measurement of fluorescent lifetimes using at least one fluorescent probe having known and/or variable fluorescent lifetimes. It is a further object of the present invention to provide the above detection and/or measurement with reduced or substantially eliminated probe photobleaching when conducting an analysis of a specimen.

It is a further object of the present invention to provide the above detection and/or measurement with reduced or substantially eliminated fluorescence background when conducting an analysis of a specimen.

It is a further object of the present invention to provide the above detection and/or measurement with reduced or substantially eliminated fluorescence background when conducting an analysis of a specimen when the background lifetime values are quantitatively similar but not identical to the measured value, based on the available resolution.

It is a further object of the present invention to provide the above detection and/or measurement with reduced or substantially eliminated fluorescence background when conducting an analysis of a specimen when the background lifetime values and measured value are both small values.

It is a further object of the present invention to provide the above detection and/or measurement with reduced or substantially eliminated autofluorescence when conducting an analysis of a specimen.

It is another object of the present invention to apply imaging techniques to three-dimensional applications for automated decision making, such as in robotics systems, spacecraft maneuvering and construction.

It is further an object of the present invention to provide remote, non-contact imaging of surfaces, such as heated or cooled surfaces for temperative imaging in ovens used for the production of semiconductors, and surfaces on which there is variable gas pressure, for example to provide imaging of local oxygen pressure in wind tunnels.

These and other objects can be achieved by the present invention which provides a method for performing two dimensional optical measurements on a subject having at least first and second physically distinguishable characteristics of interest, the method comprising the steps of: illuminating the subject with light having a first wavelength, the light being intensity-modulated at a first frequency and a first phase and adapted to produce secondary light which is intensity-modulated at a second frequency and which has a second phase; generating a gating signal which is modulated at the first frequency or a harmonic thereof, or at the second frequency, and which has a third phase differing by a detector phase angle from the first phase; receiving the secondary light and intensifying the secondary light in response to the gating signal; generating at least a two-dimensional image in response to the intensified secondary light; and detecting the two-dimensional image.

In a preferred embodiment of the present invention, the above described method is provided which further comprises synchronizing the generating of the light modulation at the first frequency and the generating of the gating signal modulation. In another preferred embodiment of the present invention, the gating frequency is a harmonic of the first frequency. In another preferred embodiment of the present invention, the gating frequency and the first frequency are identical. In another preferred embodiment of the present invention, the image generating step comprises time averaging the intensified secondary light.

In still another preferred embodiment of the present invention, the method further comprises adjusting the detector phase angle to control the two dimensional image and to suppress at least one of the first and second signals.

In still another preferred embodiment of the present invention, the second phase differs from the first phase by a target phase angle, and the method further comprises the step of shifting the detector phase angle relative to the first phase in order to selectively suppress at least one of the first and second signals and to enhance at least another of the first and second signals. The method of selectively enhancing or suppressing a desired emission is best accomplished by taking a difference between the two images obtained at two different phase angles chosen to eliminate a component in the emission.

In another preferred embodiment of the present invention, the method further comprises shifting the phase between the excitation modulation and the detector modulation in order to selectively enhance the at least one of the first and second signals and to selectively suppress at least the other of the one signal, wherein suppression of a desired component is best achieved by taking a difference of images obtained at selected phase angles.

In another preferred embodiment of the present invention, the subject comprises first and second fluorescent probes, at least one of the probes being responsive to light at the first wavelength to emit secondary light comprising fluorescent light having a fluorescence lifetime, the second phase of the secondary light being shifted from the first phase such that, when the lifetime, phase or modulation of the probe is sensitive to an analyte or chemical, the analyte or chemical can be imaged.

In another preferred embodiment of the present invention, the subject comprises first and second target areas disposed at different distances from a point where the receiving step is performed, each target area being responsive to the light at the first wavelength to reflect the light.

In another preferred embodiment of the present invention, the image is detected at a number of detector phase angles, and the images are used to construct a phase angle and/or lifetime image.

In still another preferred embodiment of the present invention, the method further comprises the steps of generating a first stored picture by setting the detector phase angle to $\pi/2$ relative to the first phase, detecting the resultant image and storing the detected image as a first picture; generating a second stored picture without modulation of the gating signal, detecting the resultant image, and storing the detected image as a second picture; generating a third stored picture by setting the detector phase angle to 0° relative to the first phase, detecting the resultant image, and storing the detected image as a third picture; subtracting the second stored picture from the first stored picture to generate a first intermediate image; subtracting the second stored picture from the third stored picture to generate a second intermediate image; and generating a ratio of the first intermediate image and the second intermediate image, the ratio identifying a pixel intensity that is proportional to the first physical property with respect to the second physical property.

In a preferred embodiment of the present invention, the above described method further comprises using the ratio to discriminate the first physical characteristic from the second physical characteristic.

According to a second aspect of the present invention, a method is provided that suppresses unwanted fluorescence from a fluorescent image of a subject, the unwanted fluorescence being generated in response to an excitation signal having a first phase, and the unwanted fluorescence having a second phase shifted from the first phase, the method comprising: generating laser light at a first wavelength; intensity-modulating the laser light at a first frequency; illuminating the subject with the modulated laser light, the modulated laser light having a first phase and being adapted to produce from the subject secondary light that is intensity-modulated at the first frequency and having a second phase; generating a gating signal modulated at the first frequency and having a third phase; defining a detector phase angle from the first phase; receiving the secondary light, and intensifying the secondary light in response to the gating signal; generating the image in response to the intensified secondary light; and adjusting the detector phase angle to eliminate from the image the signal due to the unwanted fluorescence to produce the fluorescent image.

In a preferred embodiment of the second aspect of the present invention, the subject is a fingerprint demonstrating the fluorescence image and is on a surface demonstrating the unwanted fluorescence. In another preferred embodiment of the second aspect of the present invention, the gating frequency is a harmonic of the first frequency. In still another preferred embodiment of the second aspect of the present invention, the gating frequency and the first frequency are identical.

According to a third aspect of the present invention, an apparatus is provided for performing two dimensional optical measurements on a subject having at least first and second physically distinguishable characteristics of interest, the apparatus comprising: laser means for illuminating the subject with light having a first wavelength, the light being intensity-modulated at a first frequency and a first phase and adapted to produce secondary light intensity-modulated at the first frequency and having a second phase; gating means for generating a gating signal modulated at the first frequency and having a third phase differing by a detected phase angle from the first phase; means for receiving the secondary light the means being responsive to the gating signal for intensifying the secondary light and being operative to time-average the secondary light; means for generating a two dimensional image in response to the intensified and time-averaged secondary light; and means for detecting the two dimensional image.

In a preferred embodiment of the present invention, the apparatus further comprises means for storing the detected two dimensional image, and means for image processing and analyzing the image. In another preferred embodiment of the present invention, the apparatus further comprises means for synchronizing the laser means and the gating means at the first frequency. In still another preferred embodiment of the present invention, the apparatus further comprises means for varying the detector phase angle and thereby producing respective two dimensional images.

In another preferred embodiment of the present invention, the apparatus further comprises means for analyzing plural ones of the respective two dimensional images. In still another preferred embodiment of the present invention, the laser means comprises a laser and a laser modulator operative to intensity modulate the light beam. In another preferred embodiment of the present invention, the laser means further comprises means for varying the phase difference between the first phase and the third phase for reversing the phase relation between the first and second signals.

In still another preferred embodiment of the present invention, the receiving means comprises a gated image-intensifier. Preferably, the gated image-intensifier is operative in a gated-on state and is responsive to the gating signal to provide an output demonstrating a gain modulated at the first frequency or a harmonic thereof.

In another preferred embodiment of the present invention, the apparatus further comprises microscope means for retaining the subject, the microscope means comprising an optical subsystem that is operative to direct the laser light onto the subject and to direct the secondary light to the image-intensifier.

BRIEF DESCRIPTION OF THE DRAWINGS

FIG. 5 is an illustration of the content of various signals appearing during use of the present invention.

DETAILED DESCRIPTION OF THE PREFERRED EMBODIMENTS

Figure 1:
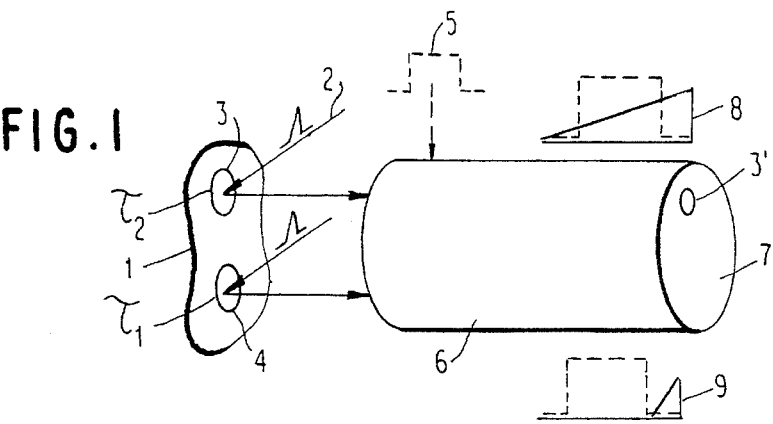
FIG. 1 is a schematic representation of a conventional pulse gating technique.

A method and apparatus have been discovered that can create lifetime multi-dimensional images using a gain-modulated intensifier. This method and apparatus provide a means to distinguish objects and to measure or detect physical characteristics of a subject (such as structural characteristics, environmental characteristics and/or the chemical composition of a subject) on the basis of the lifetime of emitted fluorescence of a bound or present fluorophore.

According to the present invention, phase-modulation and/or phase-sensitive technique also can be used to create fluorescence lifetime images in which contrast is based upon the fluorescence lifetimes rather than upon probe concentrations. The lifetimes of certain dyes are sensitive to the environment surrounding the fluorophore, and therefore, lifetime images can practically reveal the local chemical composition and details of the molecular environment which surround the fluorophore. Further, the phase-sensitive technique of the present invention can be used to provide distance-selective imaging which can be applied to many different applications such as robotics, construction, and spacecraft maneuvering.

In an apparatus and method of the present invention, a sinusoidally modulated image-intensifier is operated as a radio-frequency phase-sensitive camera, synchronized to a mode-locked and cavity-dumped picosecond dye laser. Such an image-intensifier is combined with a CCD (charge-coupled detector) camera, and, by applying digital image processing, one can obtain phase, modulation and/or lifetime images, as well as optional lifetime-selective signal suppression.

Such a method and apparatus of the present invention can utilize fluorophores which produce emissions having a known lifetime when excited by light at a predetermined wavelength and which are excitable by high-frequency intensity-modulated laser light. Detection of the fluorophore emissions from a specimen provides an image whose contrast is based upon fluorescence lifetime differences.

To generate images that have image pixel intensities dependent on probe fluorescence lifetimes, a phase-sensitive two-dimensional fluorescence detector, comprising a high-speed gated image intensifier, a low-speed two-dimensional detector, an image processor and an image monitor, is used. The image-intensifier is modulated in a periodic and approximately sinusoidal manner and operated as a radio frequency, phase sensitive camera. A high-speed laser, intensity-modulated by the output of a laser modulation driver, is used to excite the fluorescent probes in the specimen under test. A high frequency sine wave signal source also receives the laser modulation driver output and the signal source is connected to the image-intensifier gate circuit, via a variable phase shifter, to provide the sinusoidal modulation to the intensifier. If the laser is emitting periodic pulses, the intensifier's modulation frequency can be equal to the laser pulse repetition frequency, or a harmonic thereof.

The fluorescence detector according to the invention also can be used to suppress unwanted auto fluorescence. Further, by selecting proper modulation frequencies, the detector can be optimized for a variety of different probes. Also, contrast in the image can be based on fluorescence lifetime rather than intensity.

Accordingly, one object of the present invention is to provide a method and apparatus for characterizing aspects relating to the chemical composition of a specimen, which has been labeled or reacted with one or more fluorophores, on the basis of their fluorescence lifetimes which are measured by two dimensional measurements and by imaging of the fluorescence lifetimes. Another object is to provide a method and apparatus for distance-selective imaging, on the basis of back-scattered light measurements.

Methods and devices of the present invention for fluorescence lifetime imaging (FLIM) will now be described in detail with reference to the accompanying figures.

Figure 2:
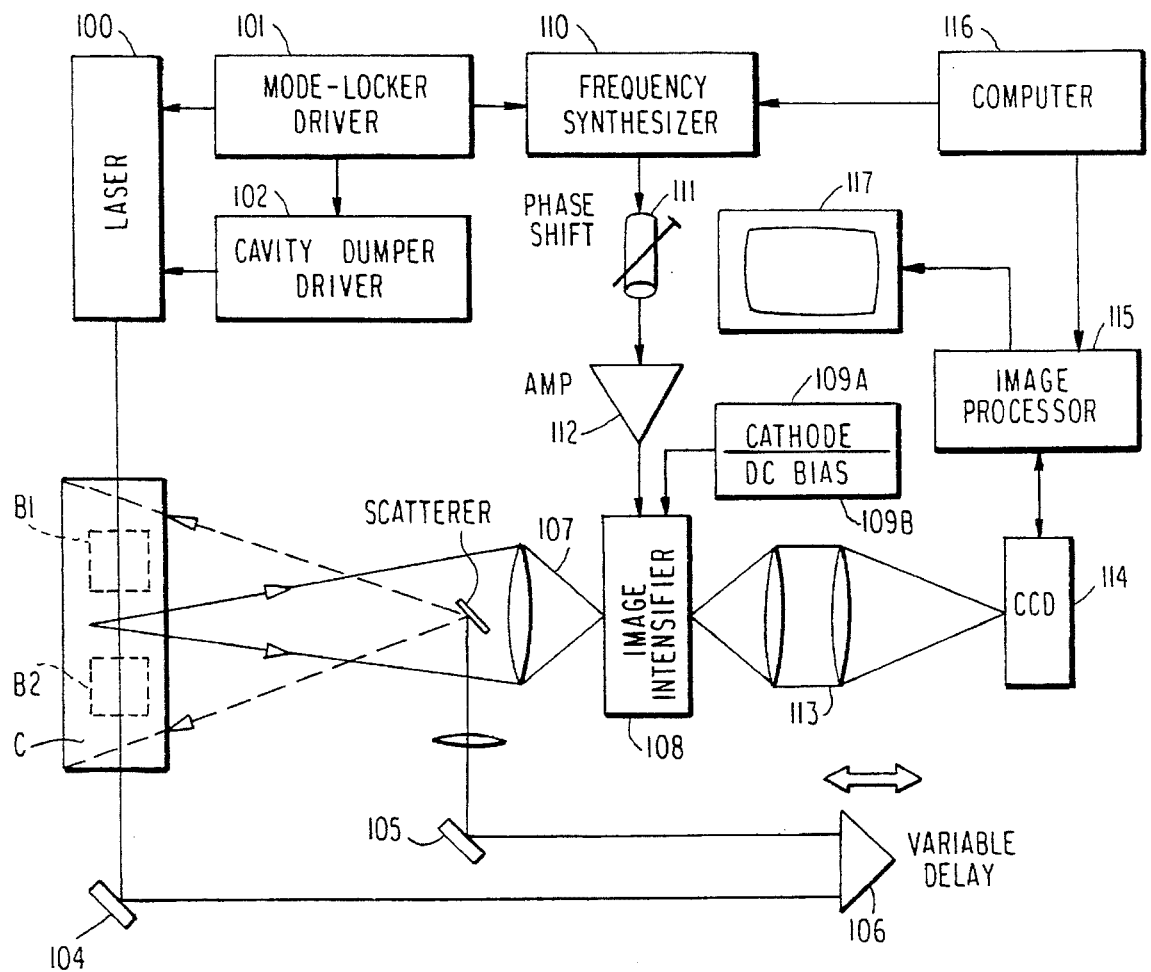
FIG. 2 is a block diagram of a first embodiment of the present invention, used for lifetime-selective detection.

FIG. 2 is a block diagram of the overall configuration of an apparatus for creating two-dimensional images in which the contrast between the images is based upon local fluorescence lifetime differences of the content of a specimen under observation. Within the specimen, objects to be discriminated from one another are tagged or dyed with suitable fluorescent substances or fluorophores having a known absorption characteristic for light within a particular range of wavelengths and emitting light at a particular wavelength. Examples of such dyes are given in Table 1 and Table 2.

TABLE 1

| Dye Type | Laser Utilized for Dye Excitation | Dye Excitation/ Absorption Wavelength | Dye Emission Wavelength |
|---|---|---|---|
| DNA-staining dyes Hoechst 33342/DAPI | Argon, Helium- Cadmium | 325–355 nm (UV) | 450 nm (blue) |
| Withramycin | Argon | 457 nm (blue-violet) | 575 nm (green) |
| Chromomycin | Argon | 457 nm (blue-violet) | 555 nm (green) |
| Propidium iodide | Argon | 342–514 nm (UV to yellow) | 615 nm (orange-red) |
| RNA-staining dyes Pyronin Y | Argon | 480–550 nm (blue-green) | 570–600 nm (orange-red) |
| DAPI | 350 | 350 nm | 450 nm |

TABLE 2

| Probe | Laser or Wavelengths | Analyte |
|---|---|---|
| Quin-2 | Pyrindium 2 dye laser (350 nm) | Calcium |
| Fura-2 | Pyrindium 2 dye laser (350 nm) | Calcium |
| Calcium green | Argon IoR Nd:Yag | Calcium |
| Calcium orange | Argon IoR Nd:Yag | Calcium |
| Calcium crimson | Argon IoR Nd:Yag | Calcium |
| PBIF, SBIF | Pyrindium 2 | $Na^+$, $K^+$ |

TABLE 2-continued

| Probe | Laser or Wavelengths | Analyte |
|---|---|---|
| SMARF-1, etc. SNAFL-1, etc. | dye laser (350 nm) R6G dye laser or Green HeNe (543 nm) | $H^+$, pH |
| Porphryrins PAH, Pyrene, 1,2 Benzanthracene | R6G or Pyrindium 2 dye laser | $O_6$ |
| Indole, tryptophane | R6G dye laser at 290 nm | $I^-$, $O_2$, sulfur compounds |

For Example, the above DNA and RNA staining dyes, as presented in Table 1, exhibit changes in their fluorescence lifetimes upon binding to nucleic acid. The method and apparatus of the present invention also provides newly discovered strategies and techniques for imaging of chromosomes. For example, the lifetime of the nucleic acid biding dye DAPI (Table 1) is known to be sensitive to the base pair (G-G, A-T) composition surrounding the binding site. Consequently, FLIM images of DAPI stained chromosomes can provide information on their local chemical composition, not heretofore possible by known techniques.

Other probes suitable for use in the present invention include those that show a sensitivity to light within a particular range of wavelengths, and which show lifetime changes in response to physical characteristics of a sample. By collecting a series of such images, each at a different detector phase, an image can be provided with contrast based on the decay time using an image processor and computer.

FIG. 2 shows a device wherein a specimen is provided containing one or more samples, such as sample B1 and sample B2, which are labeled or reactive with a fluorophore responsive to at least one physical characteristic of a sample to be detected and present in an appropriate medium C such as a liquid or gas forming a solution, emulsion, suspension or mixture.

A high-speed intensity-modulated laser (100), which emits laser light at a wavelength to which the fluorophore is responsive, directs light onto the specimen. Exemplary of a suitable modulated excitation light source to be used in an apparatus or method of the present invention is a Coherent model Antares 76-s mode-locked and frequency-doubled YAG laser, which, e.g., can pump a Coherent model 700 cavity dumped Rh6G dye laser, which provides excitation near 580 nm or frequency-doubled at 290 nm.

Such a periodically pulsed dye laser provides a light source having characteristics similar to a light source that is sinusoidally modulated at the pulse repetition frequency and at many harmonics thereof. A first optical system, which may be conventional, includes lenses (103), and mirrored surfaces (104), (105) which direct a de-focused or scattered laser beam onto the specimen. All targets are uniformly illuminated via a variable optical delay line (106) in order to introduce accurate phase shifts between the excitation modulation and the detector modulation. Upon excitation by the beam, the fluorophore tagged to the sample in the specimen under study emits a fluorescence light having a characteristic wavelength. The sample fluorescence light is focused by means of a second conventional optical system (107) onto the photocathode of a high-speed gated image intensifier (108), which may be a proximity-focused MCP image intensifier with 18 mm photocathode diameter, such as an ITT model F4111, or a Varo Model 510-5772-310 intensifier.

The laser (100) is controlled by the laser modulation driver, comprising mode-locker driver (101) and cavity dumper driver (102), connected to a modulation input port of the laser. The mode locker driver operates at a modulation frequency $f_1/2$ and causes the output of the laser to be modulated in intensity at frequency $f_1$ and harmonics thereof. A second output of the driver (101), providing a synchronization signal, is connected to a high-frequency sine wave signal source in the form of an RF frequency synthesizer (110). An RF intensifier modulation signal is generated by frequency synthesizer (110), which may be a Gigatronics Model 905 synthesizer with 1 Hz resolution and a 0.05 to 18 GHz frequency range. The synthesizer output signal is phase-locked to the laser modulation by connecting the 10-MHz clock-frequency synchronization output of the mode-locker (101) to the 10-MHz synchronization input at the synthesizer (110). The output of the signal source is connected to the input of a variable phase shifter (111) and the output of the phase shifter is connected to the gating input of the image intensifier (108). The variable phase shifter can be calibrated time delays introduced by lengths of coaxial cables, or by PTS frequency synthesizers which introduces the desired phase shift under computer control. In order to achieve proper modulation of the effective image intensifier gain, a DC bias (109B) is applied between the photocathode (109A) and the image intensifier input (108).

Alternatively, the phase shifter can be arranged within the synchronization channel between mode-locker driver (101) and synthesizer (110). In combination with the variable optical delay line (106), the effective detector phase angle can be adjusted to any desired value. The high-speed gated image intensifier (108) can be modulated directly by the +10 dBm synthesizer output signal. Additionally, an RF amplifier (112) can be added to the high-speed gated image intensifier (108) in order to obtain sufficient gain modulation, if desirable, such as in case of the ITT model.

The output frequency of synthesizer (110) is set exactly on a harmonic of the laser pulse repetition frequency, typically in the range 0.1 to 400 MHz. Frequencies below 50 MHz are obtained using PTS frequency synthesizers.

While the current measurements have been performed at MHz frequencies, such an imaging method of the present invention can also be used with for longer lifetimes of luminescent compounds or materials by utilizing lower frequencies. For example, lanthanide chelates of the type used in immunoassays display lifetimes from ms to µs, requiring frequencies in the kHz range. Charge transfer emission of the Ru-tris (i.e., phenanthroline) type displays lifetimes near 100 ns, and could be imaged with sub-MHz frequencies in a method of the present invention. Additionally, phosphorescence can display lifetimes ranging from seconds to ns, and therefore can be imaged according to the present invention with frequencies of about 1 Hz and above.

By utilizing this homodyne principle, a stationary output image is generated at the image intensifier phosphor screen. The phosphor screen is imaged by optics (113) onto a thermoelectrically cooled PM-512 CCD matrix of a Photometrics series 200 CCD camera system (114). The system has image arithmetic capabilities, provided by an image processor (115) in combination with a computer (116). A display of the image captured by the CCD camera system is provided on a CRT screen (117). It has been additionally discovered that, owing to the particular homodyne technique used, and the low CCD dark current, extremely long exposure times can be applied, which provides an unexpectedly high fluorescence detection sensitivity.

In particular, the present invention provides for tuning the output frequency of synthesizer (110) away from a harmonic of the laser pulse repetition frequency, which results in the establishment of a heterodyning mode of operation, equivalent to the homodyne regime, with a continuous detector phase shifting.

For example, when the present invention is used for production of phase sensitive imaging, the intensity of all image intensifier output pixels shows a periodical modulation at the detuning frequency offset. This principle is used to optimize the photocathode DC and RF levels for maximum linear intensifier modulation. Thus, for the use of phase-sensitive imaging in methods and devices of the present invention, the homodyne approach is preferable, but imaging methods based on the heterodye signal are also possible.

In the present invention, intensity-modulated laser light stimulates intensity-modulated fluorescence radiation. For example, where the laser (100) is modulated by a sine wave having a frequency $f_1/2$ to provide pulses at a frequency of $f_1$, the fluorescence light emitted by each of the samples $B_1$, $B_2$ also is a sine wave, modulated at a frequency $f_1$ but phase shifted relative to the excitation light by an angle $\Theta_1$. The modulation input to the image intensifier also receives an input signal at a frequency $f_1 1$, thereby providing the additional advantage of frequency synchronization throughout the system. The laser can also be modulated at $f_1$ and/or sinusoidally modulated, according to the present invention.

In the present invention, emitted light from the excited fluorophores is phase shifted relative to the excitation light from the laser (100) by an angle $\Theta_1$. The phase shift angle, $\Theta_1$, is related to the fluorescence lifetime $\tau_1$ of the corresponding fluorophore or probe.

In a fluorescence detector of the present invention, the image intensifier (108) is permanently in the gate-on state. The high frequency signal from the modulation driver, having a frequency $f_1$, is added to the gating signal causing a sinewave gain modulation within the intensifier. Since such a gain modulation is accomplished exactly at the laser modulation frequency $f_1$, the image intensifier output signal is time-independent. Since the fluorescence light is phase shifted relative to the excitation light by angle $\Theta_1$ and the detector evidences a phase angle $\Theta_D$ for gain modulation, the intensifier output signal will show a signal amplitude:

$$A = B + C*\cos(\Theta_1 - \Theta_D),$$

where B and C are constants. In order to create lifetime images, the detector phase angle $\Theta_D$ may be changed in a step-wise fashion. One picture is developed and stored for every detector phase setting. By using the image processor (115), or by using other computer processing of the images, a plurality of registered pictures can then be used for comparative analysis resulting in image contrasts.

By adjusting the detector phase angle, $\Theta_D$, to a value $\Theta_D = \Theta_1 + Pi/2$, the second, lifetime-dependent term vanishes. Thus, the lifetime-dependent image intensifier output signal of all sample pixels with a fluorescence lifetime $\tau_1$ can be made equal to 0. By subtracting of appropriately shifted phase-sensitive images, the intensity of regions with lifetimes equal to $\tau$, can be made equal to zero (FIG. 5). All probe pixels with a different lifetime, $\tau_2$, however, will generate a non-vanishing lifetime-dependent output signal because $\cos(\Theta_2 - \Theta_D)$ is not equal to 0 for $\Theta_D = \Theta_1 + Pi/2$. As a result, the difference image will show a contrast revealing region with lifetime different from $\Gamma_1$.

At the output of the image intensifier (108), the CCD camera (114) provides a reading of the image seen on the screen of the image intensifier. This two-dimensional image for the area under observation may be input to the image processor (115) for analysis in accordance with arithmetic signal processing techniques known in the art. The image processed output may be displayed for use by the operator on a fluoroscopic CRT monitor (117). Due to the fact that the detector system contains a digital image processor, many different arithmetic image procedures can be utilized to create specific lifetime images.

Figure 3:
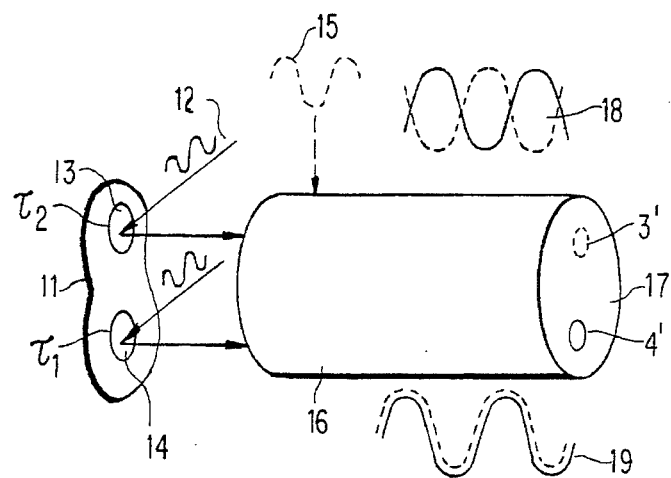
FIG. 3 is a schematic representation of the present invention.

FIG. 3 illustrates the principle of phase-sensitive imaging. Here, the fluorescent target under test is excited by laser light (12), which is sinusoidally intensity-modulated at a circular frequency, $\omega$, with a modulation degree, $m_e$. The time-dependent laser excitation power, $E(t)$ is:

$$E(t)=E_0[1+m_e \sin \omega t] \quad (1)$$

where $E_o$ is a constant power level where there is no intensity modulation. This results in a sinusoidally modulated fluorescence that is phase-shifted and demodulated relative to the excitation. For a single-exponential fluorescence decay, the phase shift angle, $\Theta_F$, depends on the decay time, $\tau$, according to the equation:

$$\tan \Theta_F = \omega \tau, \quad (2)$$

and the fluorescence modulation degree, $m_F$, is given by $$m_F = m_E[1+(\omega \tau)^2]^{-\frac{1}{2}}. \quad (3)$$

For a particular target pixel, the fluorescence optical power, $F(r,t)$, impinging onto the image intensifier (16) photocathode is $$F(r,t)=F(r)[1+m_F(r) \sin(\omega t-\Theta_F(r))] \quad (4)$$

where $F(r)$, $m_F(r)$ and $\Theta_F(r)$ are the time-averaged spatially varying optical power, and the spatially varying modulation and phase shift, respectively. The absolute value of $F(r)$ depends on many parameters, such as laser power, target absorption, target fluorescence quantum yield, and on the specific transfer functions of the optical excitation and emission systems.

In order to perform a phase-sensitive image detection, an electrical sine wave signal with a frequency equal to the laser modulation frequency is applied to the image intensifier, resulting in a time-varying gain, $G(t)$, with $$G(t)=G_o[1+m_D \sin(\omega t-\Theta_D)]. \quad (5)$$

In this equation, $G_o$ is the image intensifier gain without applying a modulating signal, and $m_D$ is gain modulation degree, caused by the modulating signal. The phase of the electrical gain modulation signal, identified by the detector phase angle, $\Theta_D$, can be shifted relative to the laser modulation phase angle in order to realize specific phase-sensitive detection modes.

Inside the image intensifier, the time-varying primary photocurrent meets a time-varying gain. Therefore, the multiplied photocurrent contains high-frequency components. However, owing to the long decay time of the image intensifier output phosphor, typically about 1 ms, all high-frequency signals are averaged at the output screen (17). The resulting time-averaged phase-sensitive optical output power, $P(r, \Theta_D)$, emerging from the corresponding pixel on the image intensifier phosphor screen, is given by the expression:

$$P(r,\Theta_D)=P_o(r)[1+(\frac{1}{2})m_F m_D \cos(\Theta_F-\Theta_D)] \quad (6)$$

with:

$$P_o(r)=\eta q(\lambda_1/\lambda_2) F(r) G_o. \quad (7)$$

Here, $\eta$ and $q$ are the quantum yields of the image intensifier photocathode and phosphor screen, and $\lambda_1$ and $\lambda_2$ are wavelengths of the target fluorescence and the image intensifier phosphorescence, respectively.

Equation 6 has been obtained by multiplying the time-varying fluorescence (Equation 4) by the time-varying intensifier gain (Equation 5), and taking into account the averaging effect of the intensifier phosphor screen. It can be seen that the time-averaged image intensifier output power (Equation 6) depends on the phase relation between the modulated fluorescence and the modulated intensifier.

Referring for the moment to FIG. 3, different phase relations for two fluorescent areas, such as $\tau_1$, $\tau_2$ in FIG. 3, can be seen. Because the lifetime $\tau_1$ is assumed to be very short, the generated photocurrent $S(\tau_1, \Theta_D)$ is nearly in-phase with the detector modulation. On the other hand, because $\tau_2$ is a long lifetime, the second photocurrent component $S(\tau_2, \Theta_D)$ is out-of-phase. These phase relations can be reversed by introducing an additional phase shift between the excitation modulation and the detector modulation. Therefore, either the short-living component $\tau_1$ or the long-living component $\tau_2$ can be adjusted to be out-of-phase. This feature provides a significant advantage with respect to the conventional pulsed intensifier modulation.

From Equation 6, different modes of operation for phase-sensitive imaging can be derived. Assuming unwanted fluorescence or autofluorescence with a lifetime $\tau_U$ has to be suppressed in an image, the unwanted fluorescence displays a phase shift, $\Theta_U$, relative to the excitation signal phase, given by the expression:

$$\Theta_U=\arctan (\omega \tau_U). \quad (8)$$

In one of the various potential modes of operation, a first image is taken at a detector phase angle setting:

$$\Theta_D=\Theta_U-\pi/2 \quad (9)$$

and stored in a digital image processor. Then, the image intensifier modulation is turned off, a second image is taken which is stored in the image processor memory, and subtracted pixel by pixel from the image stored first. The described procedure results in an image corresponding to an effective image intensifier output pixel power, $P_{eff}(r)$, with:

$$P_{eff}(r)=(\frac{1}{2})P_o(r)m_F m_D \cos(\Theta_F-\Theta_U+\pi/2). \quad (10)$$

From Equation 10 it can be seen that in the image generated by this procedure, fluorescence with a phase angle $\Theta_F=\Theta_U$, or with a lifetime $\tau=\tau_U$, is completely suppressed. Fluorescent target pixels having a lifetime $\tau<\tau_U$ cause a positive image pixel intensity, and target pixels with $\tau>\tau_U$ cause a negative image pixel intensity. By adjusting the detector phase angle, $\Theta_D$, and by reversing the image subtraction sequence, this procedure can be used to suppress unwanted fluorescence of any lifetime. It also can produce positive image pixel intensities for the fluorescence of interest with lifetimes longer or shorter than $\tau_U$. According to Equation 10, the image pixel intensity is proportional to $\sin (\Theta_F-\Theta_U)$. This means the pixel intensity increases with increasing difference between $\tau$ and $\tau_U$. Therefore, this mode of operation yields fluorescence lifetime images, starting with an intensity equal to zero for the suppressed component. If the lifetime of the fluorescence of interest is very close to $\tau_U$, maximum lifetime selectively can be achieved by optimizing the laser modulation and image intensifier modulation frequency. The optimum modulation frequency for maximum lifetime selectivity, $f_{opt,\Delta\tau}$, is given by the expression:

$$f_{opt,\Delta\tau}=(\sqrt{2}2\pi\tau_U)^{-1}. \quad (11)$$

A second mode of lifetime-selective signal suppression is illustrated in FIG. 5. Assume the fluorescence component with the longer lifetime, $\tau_2$, is the unwanted one which has to be suppressed. In this mode, two images are taken at two detector phase angles that differ by 180° ($\pi$-shift); for example, at the detector phase angles indicated by the arrows A and B. Then, the stored images are subtracted, i.e. $\Delta S (\tau_1)=S_A-S_R$. In order to obtain a maximum image contrast, the two detector phase angles are selected so that for both settings the image pixel intensity for the unwanted fluorescence is the same as with the nonmodulated image intensifier. Owing to the subtraction function, the equal pixel intensities obtained at both settings cancel out in the processed image; i.e. $\Delta S (\tau_2)=0$. Thus, by subtracting the stored images pixel-by-pixel, the processed intensity becomes equal to zero for all target pixels emitting with fluorescence lifetime $\tau_2$. The processed pixel intensity for the fluorescence of interest obtained by this y-shift method allows for a higher contrast; i.e. $\Delta S (\tau_1)=2S_A$.

In a third mode of operation, three images are taken. For the first image, $\Theta_D$ is set to $\pi/2$ relative to the laser modulation phase. According to Equation 6, the optical output power emerging from a pixel on the image intensifier phosphor screen is now:

$$P_1(r)=P_o(r)[1+(\frac{1}{2})m_F m_D \sin \Theta_F]. \quad (12)$$

The second image is taken with no intensifier modulation applied. In this case, Equation 6 yields for the intensifier pixel power:

$$P_2(r)=P_o(r). \quad (13)$$

The third image is taken at a detector phase setting O relative to the laser modulation phase, resulting in an intensifier pixel power:

$$P_3(r)=P_o(r)[1+(\frac{1}{2})m_F m_D \cos \Theta_F]. \quad (14)$$

By subtracting image 2 from image 1 and subtracting image 2 from image 3, two intermediate images, 1' and 2' are obtained. If now the ratio of the images 1' and 2' is generated, the resulting pixel intensity is given by the expression:

$$P_4(r)=\sin\Theta_F/\cos\Theta_F=\tan\Theta_F=\omega\tau_F. \quad (15)$$

This equation shows that now the processed pixel intensity is directly proportional to the fluorescence lifetime. By adjusting the two detector phase settings to angles that are different from $\pi/2$ and 0, this mode of operation can also be combined with lifetime-selective fluorescence suppression. According to Equation 15, the processed pixel intensity is independent of $P_o(r)$, i.e. independent of the target fluorescence quantum yield. This is not the case with the two modes previously discussed. Therefore, additional information concerning the target fluorescence quenching can be obtained by combining the third operational mode with the first or the second operational modes.

In a fourth mode of operation, a series of images is taken at a set of detector phase angles, covering approximately the range 0–2$\pi$. All images are stored, and for each the phase-sensitive intensity is fit to Equation 6. From this fitting procedure, the fluorescence phase shift $\Theta_F$ and/or the apparent lifetime $\tau_F$ according to Equation 2 is obtained; these can be used to create fluorescence lifetime images.

Figure 6A:
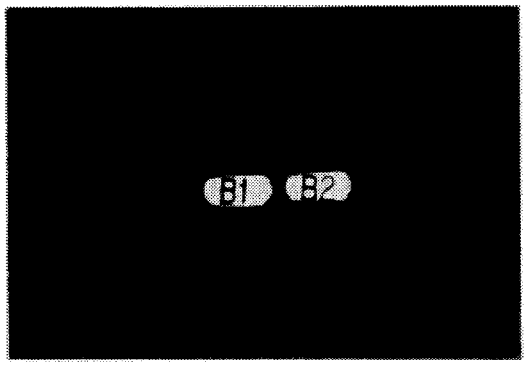
FIG. 6(A)–6(C) illustrates the use of lifetime selective images.
Figure 6B:
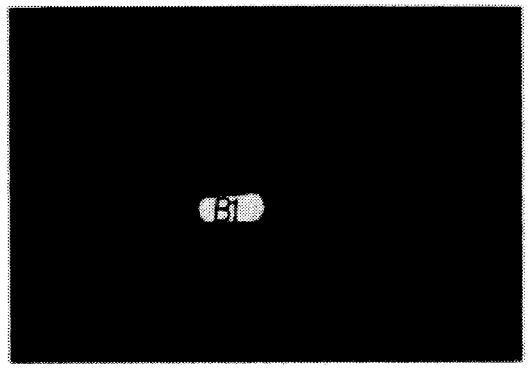
Figure 6C:
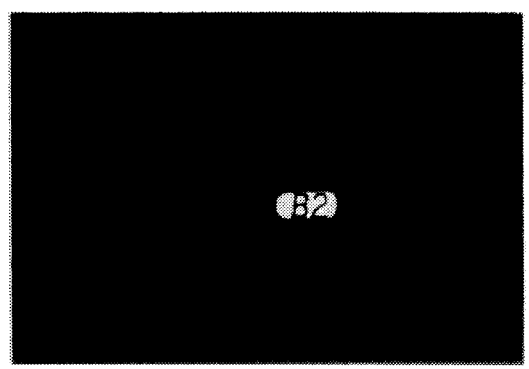

FIGS. 6A, 6B and 6C illustrate lifetime-selective fluorescence imaging, using the apparatus of FIG. 2, for samples $B_1$, $B_2$ containing fluorophores with different lifetimes. In this example, Rhodamine 6G in water with a lifetime of 4 ns, and Rhodamine B in water with a lifetime of 1.5 ns are used. FIG. 6A is obtained with no modulation applied to the intensifier (108) of FIG. 2. Both samples exhibit nearly equal fluorescence intensities. The images in FIG. 6B and 6C were created using the procedure illustrated in FIG. 5, and described above as the second mode of lifetime-selective signal suppression. As can be seen, complete suppression of either the Rhodamine 6G emission or the Rhodamine B emission is attainable. A further increase of the contrast is possible by applying appropriate pixel intensity windowing. For the images shown in FIG. 6B and 6C, small residual emissions may be used to indicate the location of both samples.

Figure 4:
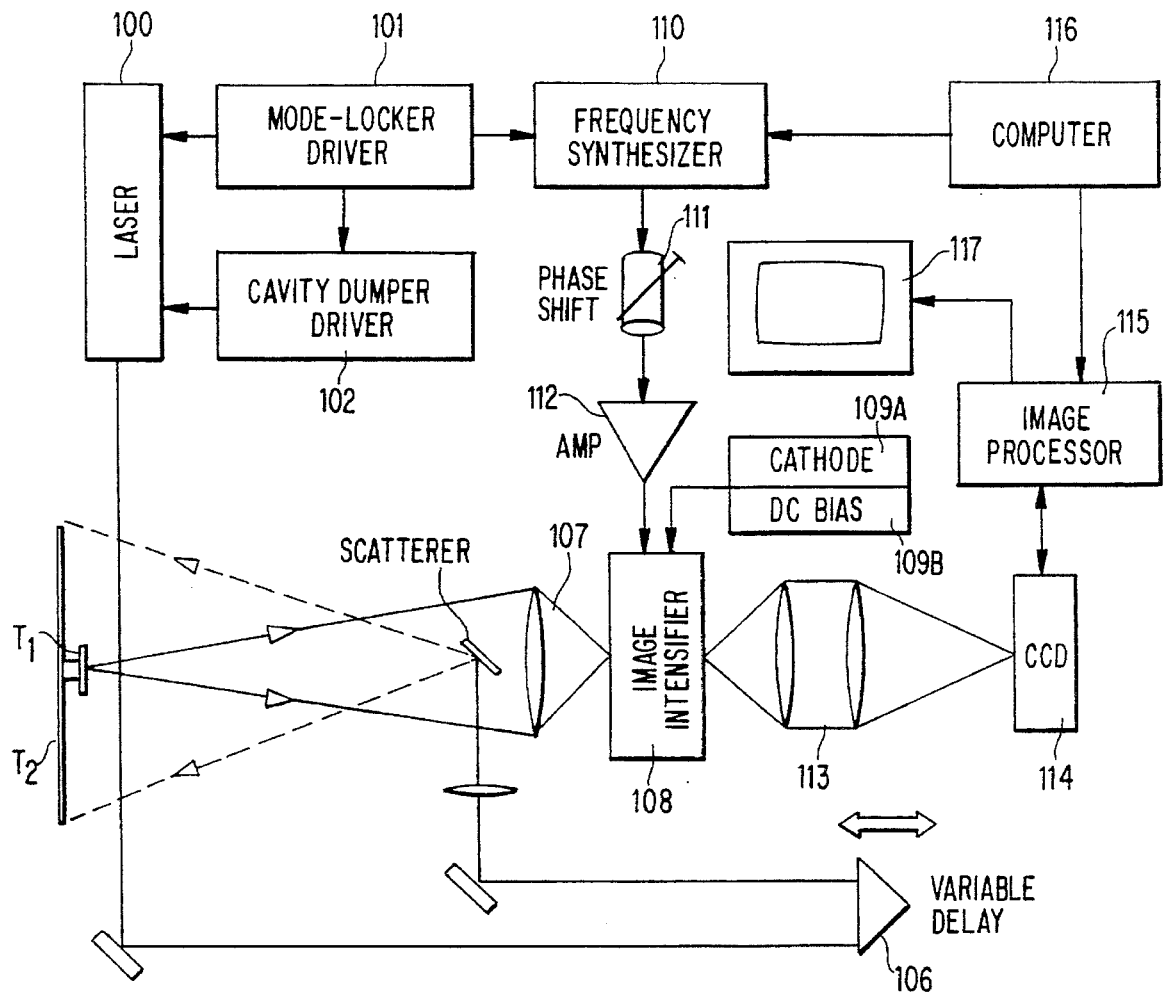
FIG. 4 is a block diagram of a second embodiment of the present invention, used for distance selective detection.
Figure 7A:
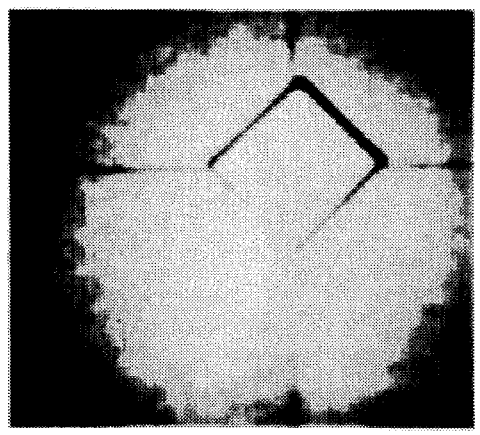
FIG. 7(A)–7(C) illustrate the use of distance selective images.

Distance resolution is obtainable with phase-sensitive imaging on back-scattering targets. As indicated in FIG. 7A, the same system as seen in FIG. 2 is used, however the samples are replaced by a three-dimensional target, which is a large flat surface, with a central quadratic plateau. The plateau (118) shown in FIG. 4 has a height of 3.75 cm. The flat surface of this target corresponds to a large fluorescent area of a first short lifetime, and the central quadratic area corresponds to a second lifetime which is shorter than the first by only 0.25 ns. As with the fluorescent materials in FIG. 6A–6C, the image shown in FIG. 7A has been obtained without image intensifier modulation. Both the large and the small central area show a comparable intensity level.

Figure 7B:
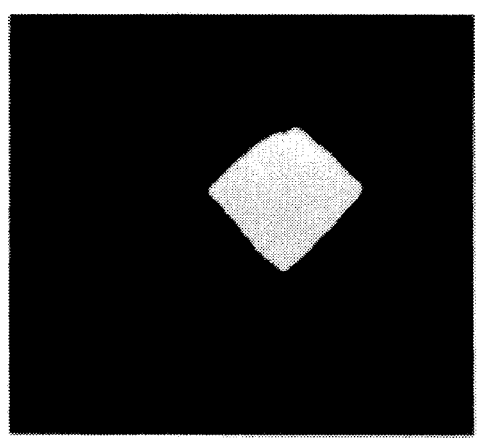
Figure 7C:
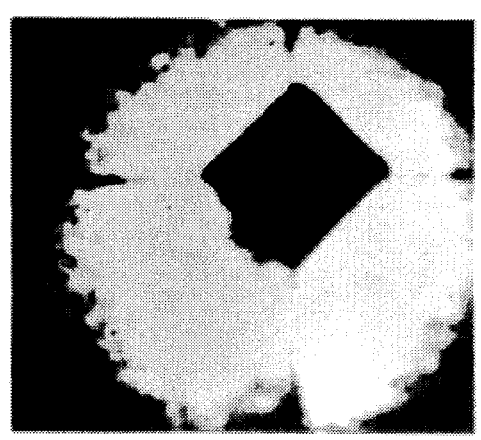

The images in FIGS. 7B and 7C demonstrate distance-or lifetime-selective signal suppression. In both, the second mode of signal suppression according to FIG. 5 was used, supplemented by additional pixel intensity windowing. As becomes evident from these images, total signal suppression with a distance resolution of 3.75 cm, or with a lifetime resolution of 0.25 ns can be established. Moreover, complete reversal of the black-and-white contrast can be realized by choosing suitable detector phase settings according to FIG. 5. Compared to the non-modulated image intensifier (FIGS. 6A and 7A), no noticeable reduction in the spatial resolution was observed for the central phosphor screen area. Close to the screen edge, however, the spatial resolution may be reduced slightly.

Image intensifier modulation frequencies up to at least 600 MHz may be used. With increasing frequency, a reduction in the intensifier modulation degree and a phase shift between the center and the edge is observed on the phosphor screen. These artifacts can be overcome by using synthesized reference targets, and applying suitable image processing correction methods.

Sinusoidally modulated image intensifiers, and CCD cameras are easily integrated into fluorescence microscopes in order to performphase-sensitive imaging on biological samples. In order to allow for an extreme high fluorescence detection sensitivity, the homodyne method is rather straightforward. Moreover, a variety of specific modes of operation can be used directly. The heterodyning approach does not require phase shifters and can be extended, to allow more precise measurements due to frequency filtering. By utilizing repetitive multi-exposures, a detection sensitivity comparable to the homodyne method is attainable.

The method and apparatus of the present invention also may be useful for remote temperature imaging during manufacturing processes, .such as semiconductor manufacture. In such application, the fluorophore may be sprinkled on the object of interest or embedded in its matrix, the local decay time of the fluorophore would reveal the local temperature.

In addition, a method and apparatus of the present invention can be used for local pressure sensing on surfaces, such as by using fluorophores whose lifetimes are sensitive to local oxygen pressure.

Clearly, the tendency of fluorophores to bleach rapidly as a result of irradiation will have no effect on the analysis performed by the disclosed apparatus. Photobleaching and variable concentration has no effect on the lifetime of the fluorophores or their measurement. Thus, an analysis of the specimen related to particular fluorophores can be conducted notwithstanding variations in these factors. In fact, sensitivity of fluorophore decay times to the physical and chemical environment make it possible to characterize the chemical and physical properties of the specimens.

Finally, measurements on flat backscattering targets tilted by defined angles also can be performed. Tilting of objects around two orthogonal axes can be measured remotely by using high-frequency phase-sensitive imaging. In order to establish maximum tilting resolution, the image intensifier modulation frequency can be optimized for maximum distance resolution. This option has the potential for many applications, for instance in robotics, construction, and even in spacecraft maneuvering.

The following are examples (in addition to the examples presented above which include data presented in FIGS. 6(A)–6(C) and 7(A)–7(C)) of fluorescence lifetime imaging according to the present invention.

As suitable standards for FLIM according to the present invention, as used below in the following examples, FIGS. 14(A)– 14(B) present three-dimensional (3D) and two-dimensional (2D) data plotting phase angle in degrees for standards POPOP, perylene and 3-AFL, correpsonding to fluorescence lifetimes. FIGS. 15(A)–15(B) present 3D and 2D data plotting decay time in nanoseconds, based on change in modulation (FIGS. 17(A)–17(B) vs. pixel for POPOP, perylene and 3-AFL. FIGS. 16 (A)–16(B) present 3D and 2D data plotting decay time, based on phase (FIGS. 14(A)–14(B)), vs. pixel for POPOP, perylene and 3-AFL. FIGS. 17(A)–17(B) present 3D and 2D data plotting modulation in percent for standards POPOP, perylene and 3-AFL, corresponding to fluorescence lifetimes.

Figure 14:
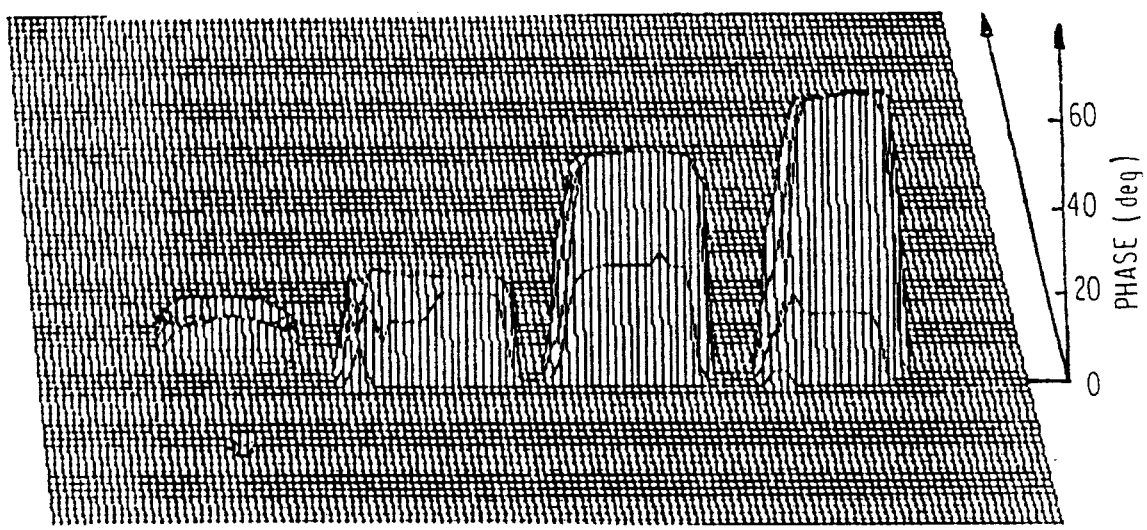
FIG. 14(A) and 14(B) are respectively 3D and 2D graphical representations of fluorescence standards for fluorescence phase-imaging at $F_{MOD}=37.999$ MHz, for phase angle (in degrees) vs. pixel vs. horizontal image for a scatterer, POPOP, perylene and 3 - AFL.
Figure 14:
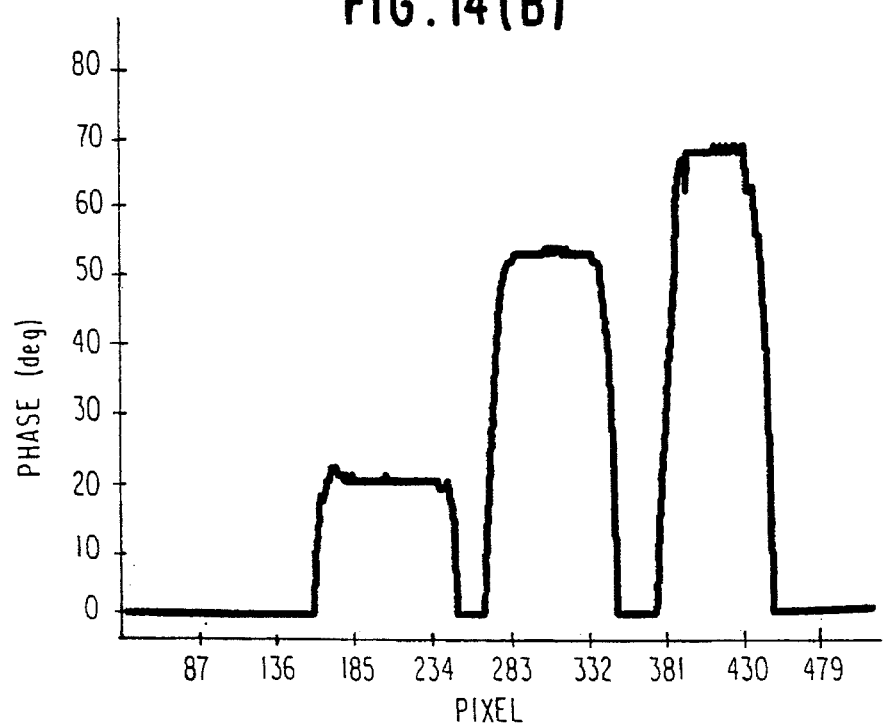
Figure 15A:
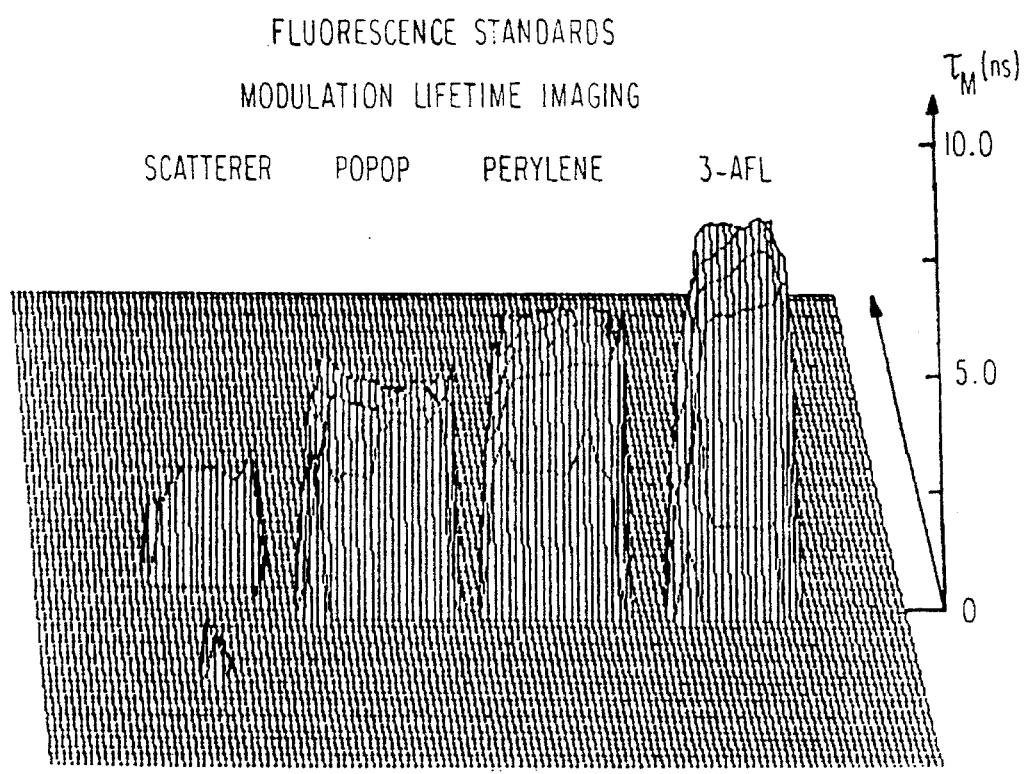
FIG. 15(A) and 15(B) are respectively 3D and 2D graphical representations of fluorescence data images of standards, wherein modulation lifetime is plotted vs. pixel for a scatterer, POPOP, perylene and 3 - AFL.
Figure 15B:
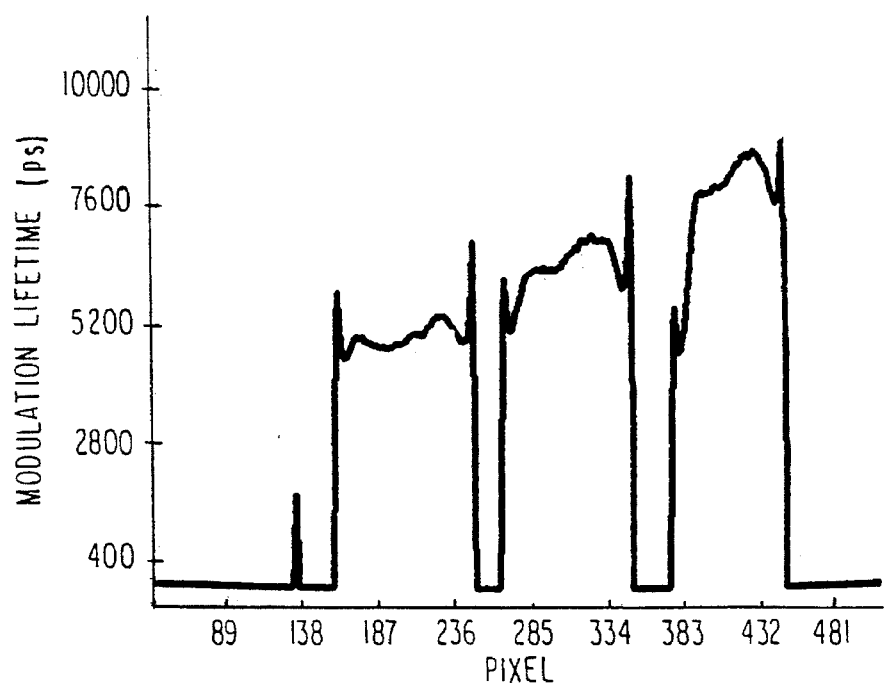
Figure 16A:
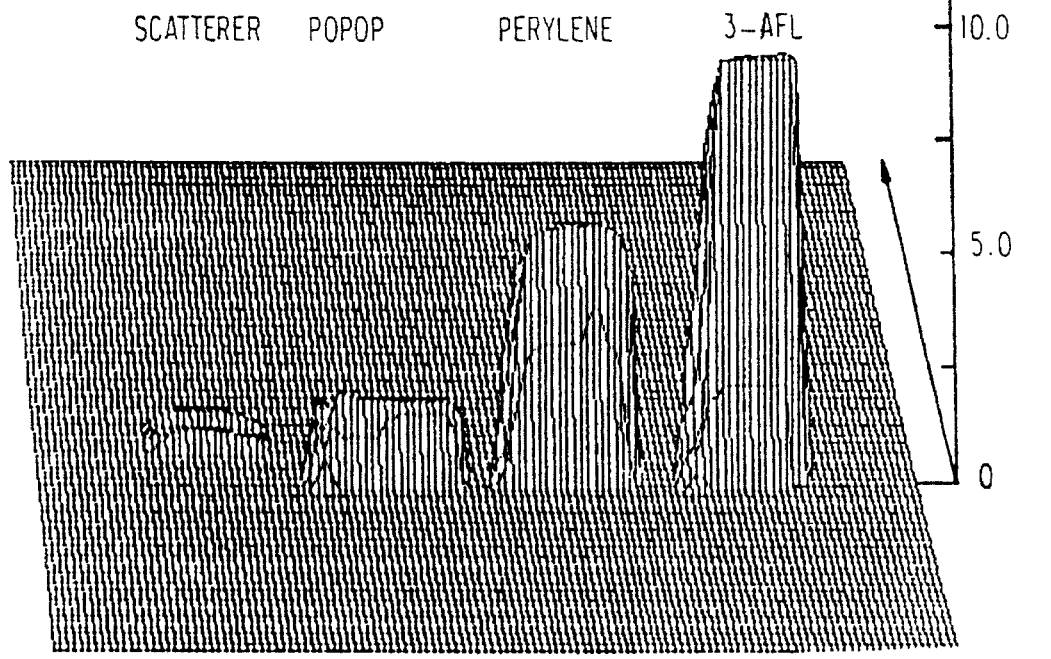
FIG. 16(A) and 16(B) are respectively 3D and 2D graphical representations of fluorescence standards using phase lifetime imaging, wherein the phase lifetime is plotted vs. pixel for a scatterer, POPOP, perylene and 3 - AFL.
Figure 16B:
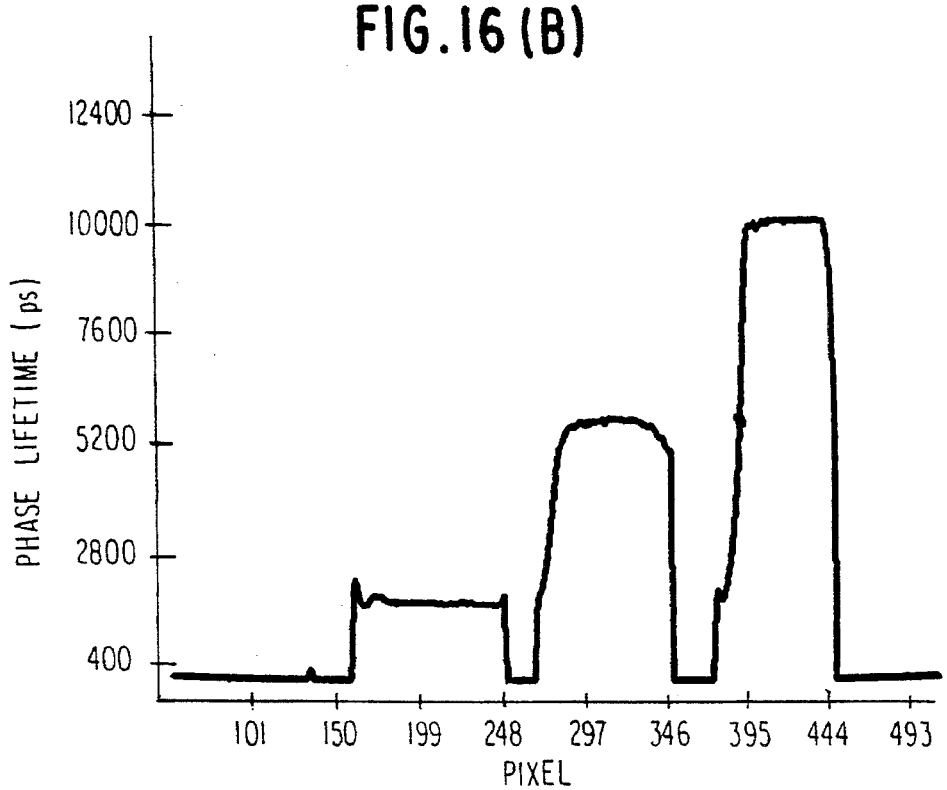
Figure 17A:
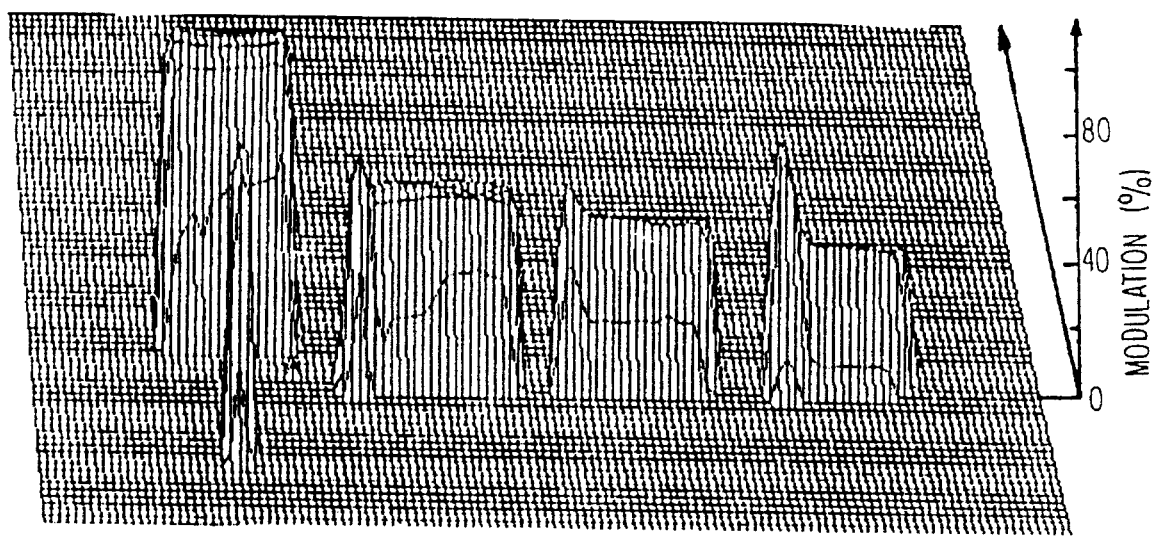
FIG. 17(A) and 17(B) are respectively 3D and 2D graphical representations of modulation imaging at $F_{MOD}=37.99$ MHz, wherein percent modulation is plotted vs. pixel for a scatterer, POPOP, perylene and 3 - AFL.
Figure 17B:
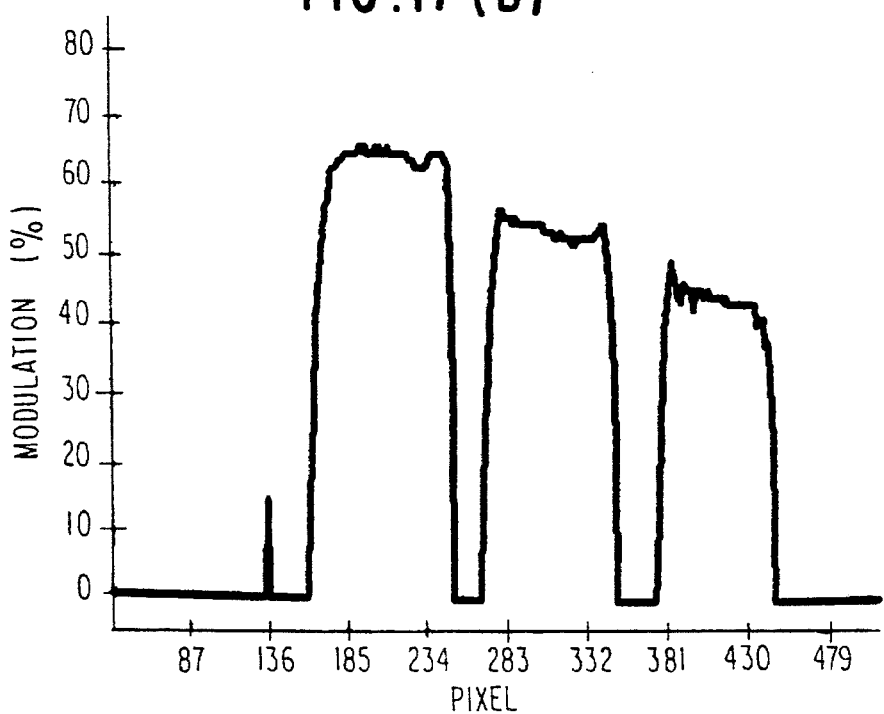

Accordingly, FIGS. 14–17 show fluorescence imaging of fluorescence standards POPOP, perylene and 3-AFL, showing change in phase angle (deg) (FIGS. 14(A)–14(B)), modulation lifetime (ps) (FIGS. 15(A)–15(B)); phase lifetime (ps) (FIGS. 16(A)–16(B)); and change in percent modulation (%) (FIGS. 17(A)–17(B)).

EXAMPLE 1: FLUORESCENCE LIFETIME IMAGING OF NADH, POPOP AND NADH+ EXCESS OF MALATE DEHYDROGENASE

METHODS. The samples to be measured according to the present invention (as shown schematically in FIG. 8) consisted of rows of cuvettes (203), containing a standard fluorophore POPOP, NADH alone or NADH with an excess of malate dehydrogenase.

Figure 8:
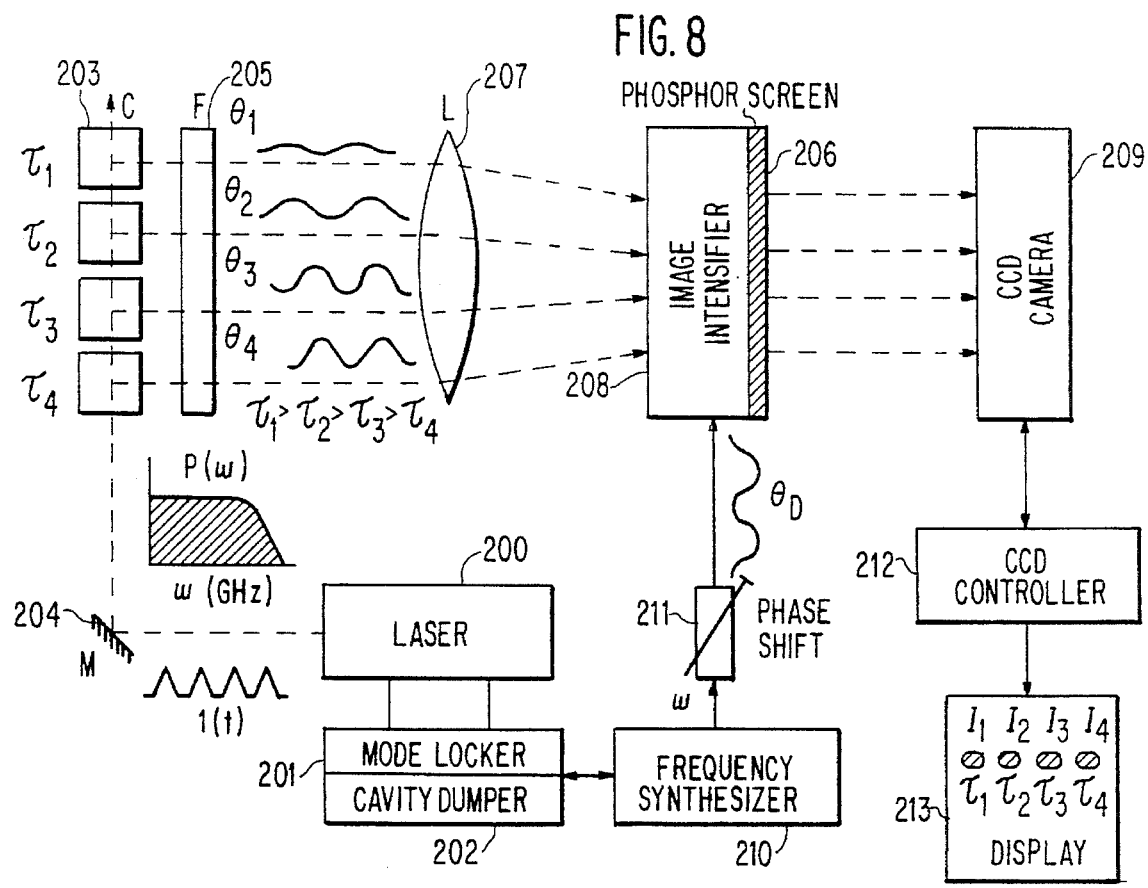
FIG. 8 is a schematic representation of apparatus for fluorescence lifetime imaging (FLIM).

According to FIG. 8, the light source was a picosecond dye laser (200) consisting of a mode-locked Antares NdYAG, which synchronously pumps a cavity-dumped pyridine-1 dye laser, frequency-doubled to 355 nm, with a pulse repetition rate of 3.7999 MHz, driven by a frequency synthesizer (210) via a mode locker (201) and a cavity dumper (202). The resulting emitted excitation laser light from the modulated laser (200) was reflected off a mirror (204) and the laser light was thus emitted through the center of the cuvettes (203). The emission was then isolated from the excitation using a Corning 3-75 filter (205), which transmits light above 385 nm, and then passed through a lens (207).

The detector was a CCD camera (209) from Photometrics (series 200) with a thermo-electrically cooled PM-512 CCD controller (212). The gated image intensifier (208) (Varo 510– 5772-310) with a phosphor screen (206) was positioned between the cuvettes (203) and the CCD camera (209). The intensifier gain driven by the frequency synthesizer (210) was modulated via a phase shift (211) by a RF signal applied between the photocathode and microchannel plate (MCP) input surface (see Lakowicz and Berndt *Rev. Sci. Inst.* 62:1727–1734 (1991)). Phase delays were introduced into this gating signal using calibrated coaxial cables via the phase shift (211). A CCD controller provided a signal to the display (213) for providing an image showing a change in decay time, phase angle or modulation of the emitted luminescence corresponding to a change in luminescence lifetime of the sample.

Lifetimes recovered from the FILM measurements were compared with those obtained using frequency-domain (FD) measurements and instrumentation (Lakowicz and Mallival *Biophysical Chem.* 21:6178(1985); Lakowicz et al *Rev. Sci. Inst.* 57:2499–2506 (1986); Laczko et al *Rev. Sci. Inst.* 61:2331–2337 (1990). For the FLIM measurements polarizers were not used to eliminate the effects of Brownian rotation. NADH was obtained from Sigma and pig heart malate dehydrogenase was from Boehringer, and were dissolved in 100 mM MOPS buffer, pH 7.0. The concentrations were $2\times10^{-5}$M (HC) and $1\times10^{-5}$M (LC) for NADH alone and $1\times10^{-5}$M NADH with $2\times10^{-5}$M malate dehydrogenase. POPOP was dissolved in cyclohexane. The temperature was room temperature, near 24° C.

Figure 9:
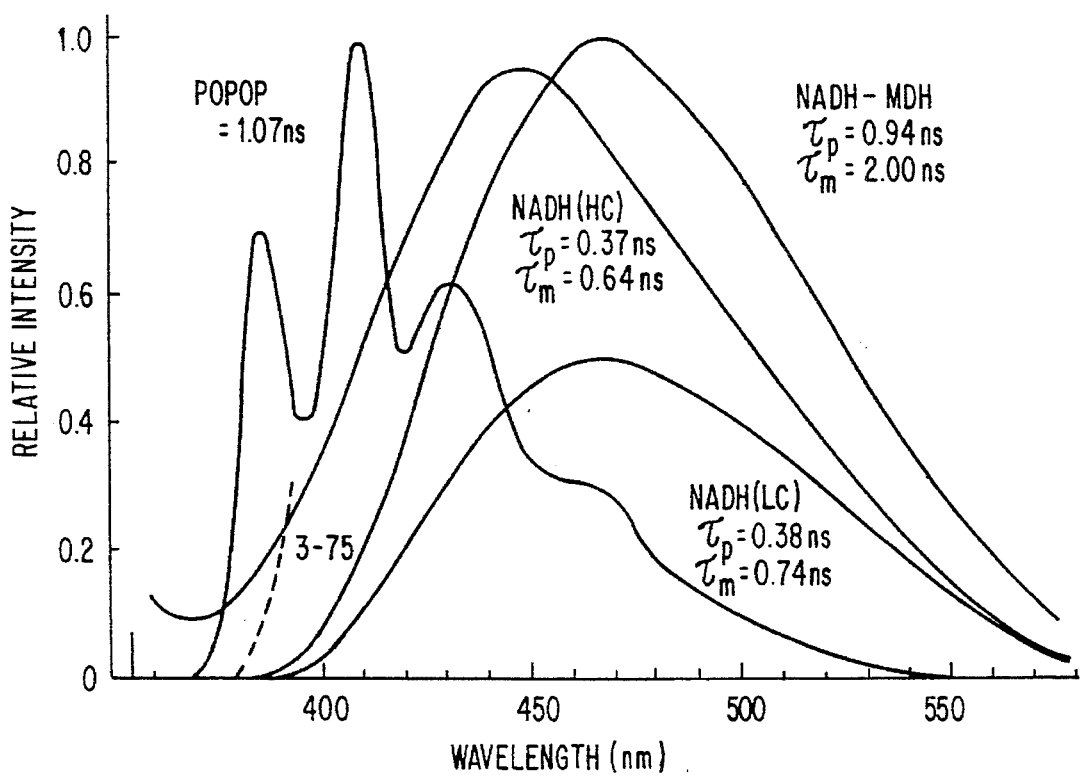
FIG. 9 is a graphical representation of emission spectra of four samples used for FLIM.

RESULTS. Emission spectra of the test samples for FLIM are shown in FIG. 9. The structured emission is for POPOP, which was used as a reference fluorophore with an independently measured lifetime of 1.07 ns (Table 3, below). The emission from unbound NADH is unstructured with a maximum near 470 nm. Binding of NADH to malate dehydrogenase (MDH) results in a 2-fold increase in the NADH intensity, which is typical for NADH binding to a dehydrogenase. Two different solutions of NADH were used. In one (LC) the NADH concentration was identical to its concentration when bound to MDH. In the second, the NADH concentration was two-fold higher (HC) in order to match the intensity of the MDH-NADH solution.

Comparative results for lifetimes of these solutions were measured using known frequency-domain instrumentation (Lakowicz and Malival *Biophysical Chem.* 21:61–78 [1985]; Lakowicz et al *Rev. Sci. Inst.* 57:2499–2506 [1986]; Laczko et al *Rev. Sci. Inst.* 61:2331–2337 [1990]) at a modulation frequency close to that used for the FLIM measurement (Table 3, below). The unequal phase and modulation lifetimes indicated that the NADH intensity decay was not a single exponential, as is known to be the case for free NADH (Visser et al *Photochem. Photobiol.* 33:35–40 [1981].

The four solutions, three with NADH and one containing POPOP, were placed in four cuvettes and excited with the 355 nm laser beam, as shown in FIGS. 10(A)–10(E). The phase-sensitive images were collected at a number of detector phase angles. Representative images are shown in FIGS. 10(A)–10(D), which show the 2D images from the illuminated solutions, and a tracing of the intensity measured for a line across the image (FIG. 10(E)). Also shown in FIGS. 10(A)–10(D) are 3D projections in which the horizontal plane represents the position and the height represents the phase-sensitive intensity. The phase-sensitive intensities were found to be strongly dependent upon the detector phase angle.

Figure 10A:
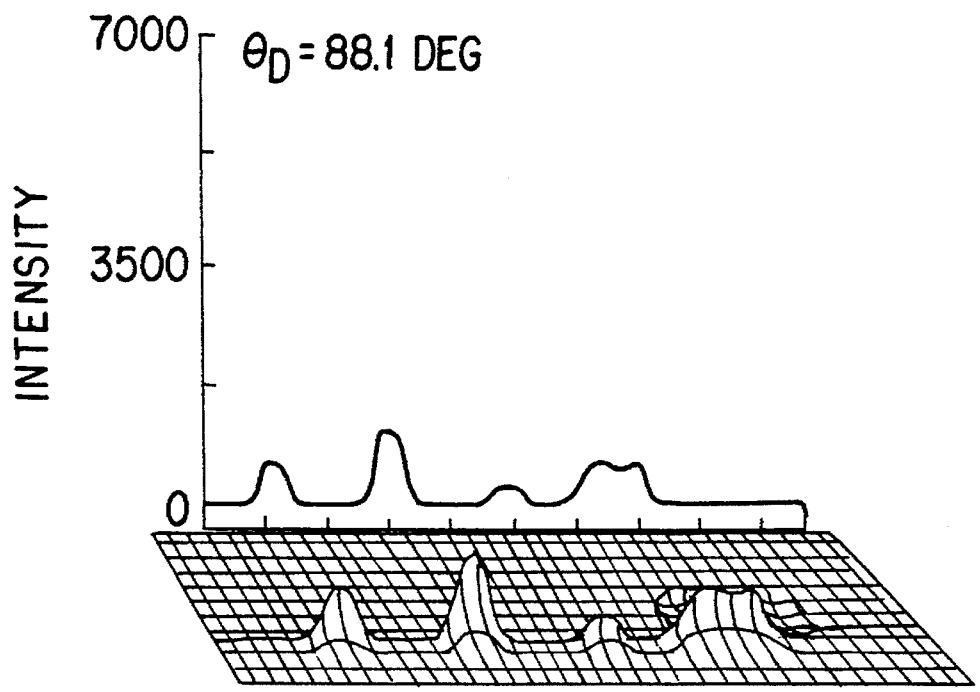
FIG. 10 (A) to 10(D) are graphical representations of phase-sensitive fluorescence data images of the four samples.
FIG. 10(E) is a graphical representation of phase-sensitive intensities of the central illuminated region of each sample.
Figure 10B:
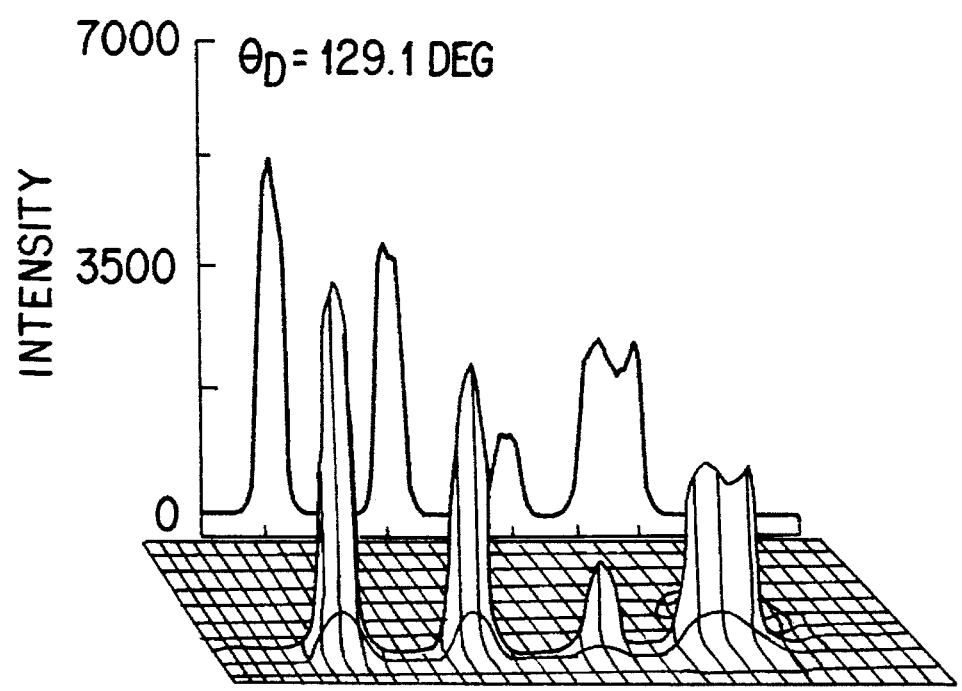
Figure 10C:
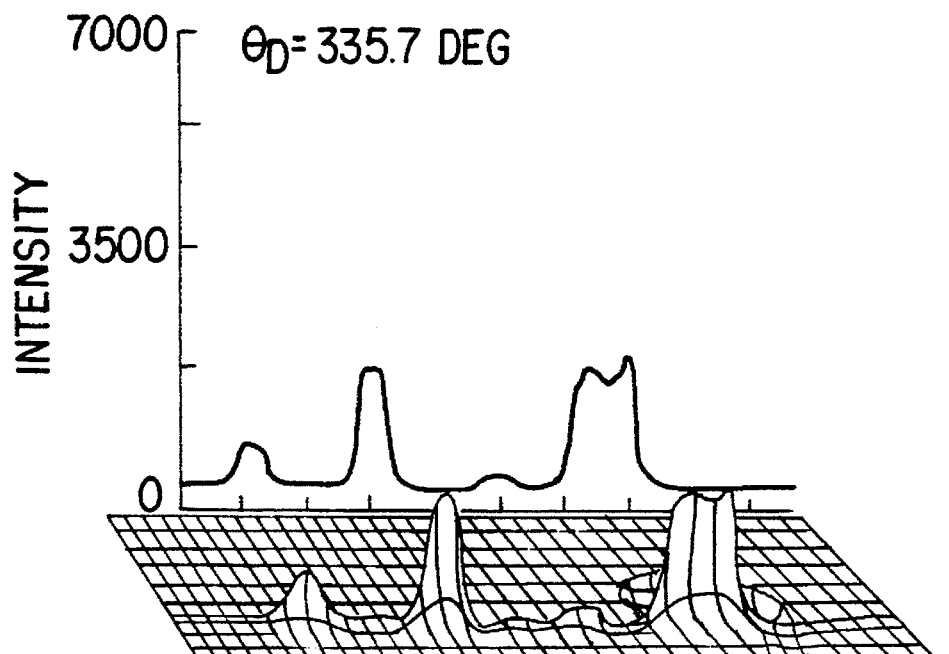
Figure 10D:
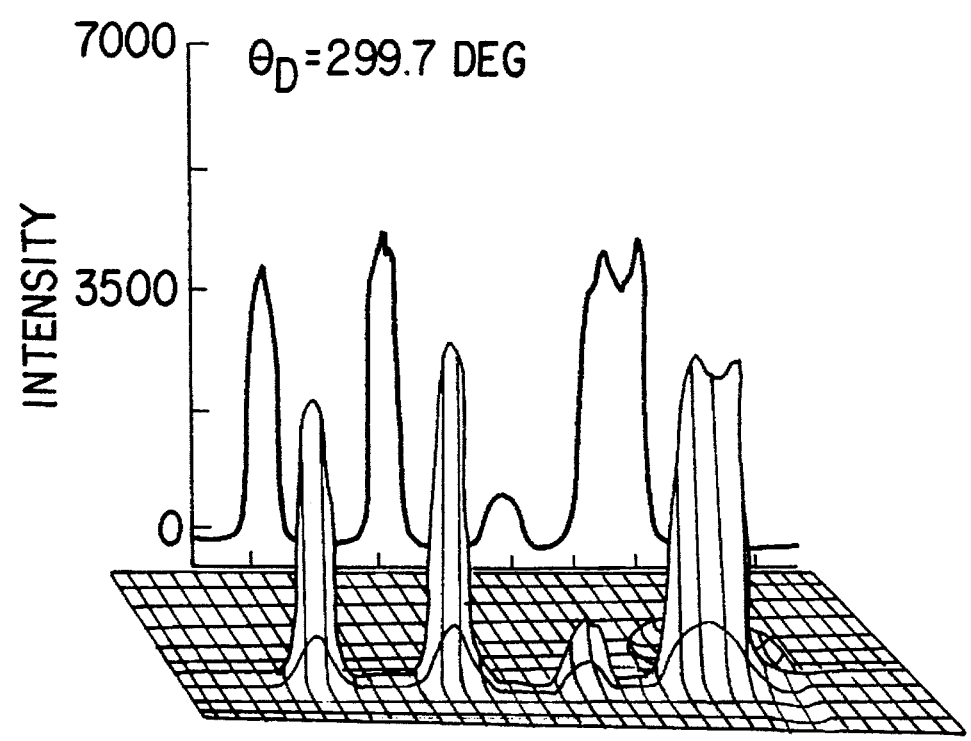
Figure 10E:
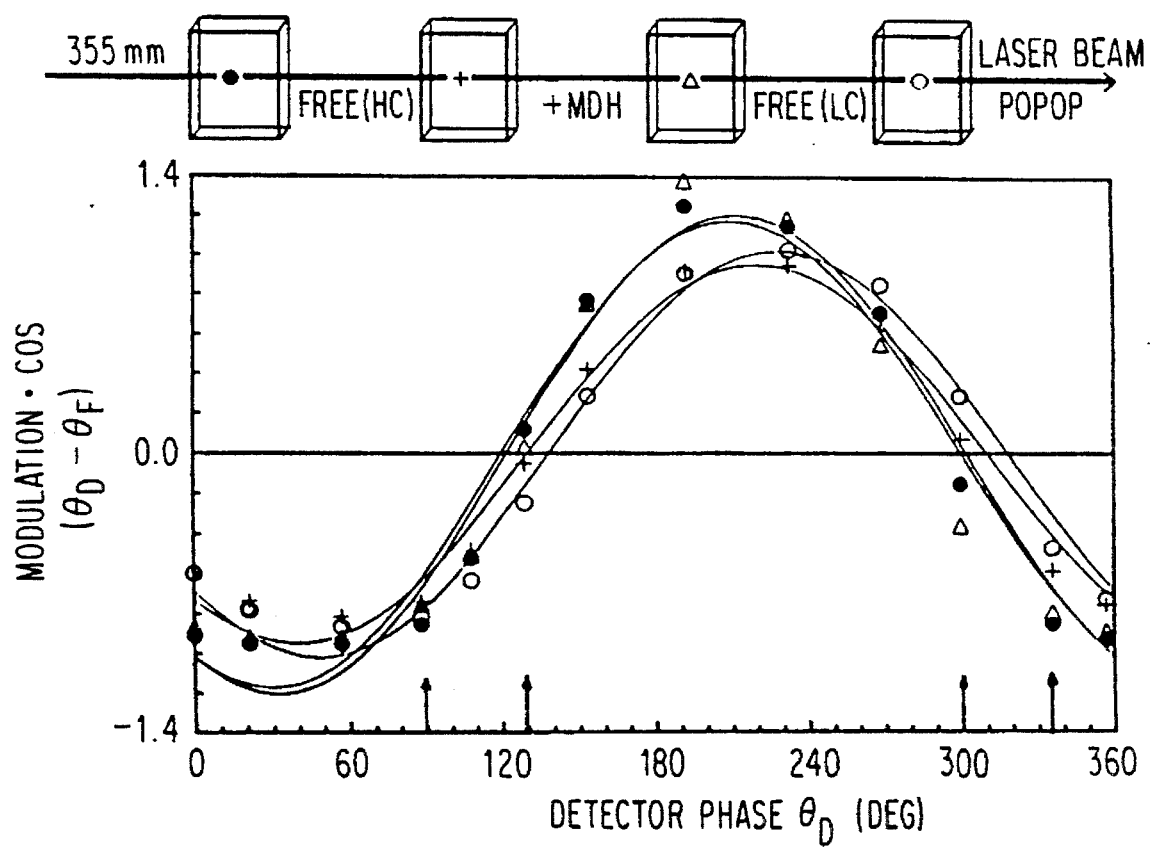

The phase sensitive intensities are expected to vary as the cosine of the detector phase angle. The phase sensitive intensities of the central illuminated region of each cuvette were fit to a cosine curve (FIG. 10(E)) and the resulting phase shifts are summarized in Table 3 below. FIG. 10(E) shows that the phase angles are nearly identical for the two solutions of unbound NADH (°, Δ). A larger phase shift was found for MDH-bound NADH (+), as is expected from the longer decay time (Table 3, below). The phase angle of POPOP is still larger due to its 1.1 ns lifetime. The phase angles from the central position in the phase-sensitive images are in good agreement with those obtained from the frequency-domain measurements (Table 3, below).

Figure 11A:
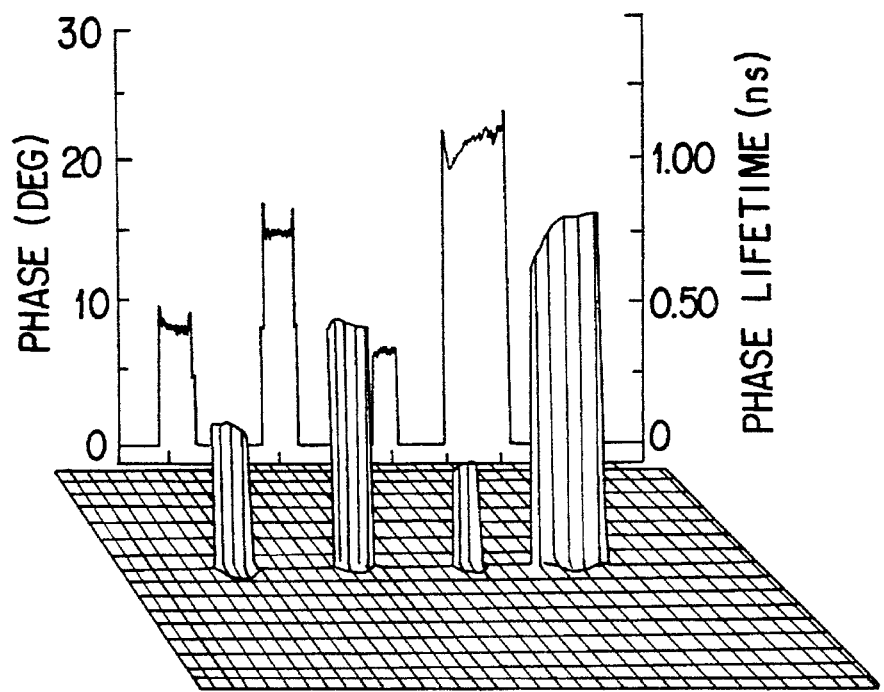
FIG. 11(A) and 11(B) are graphical representations of phase-modulation and lifetime data images of free and bound nicotinamide adenine dinucleotide, reduced from (NADH).
Figure 11B:
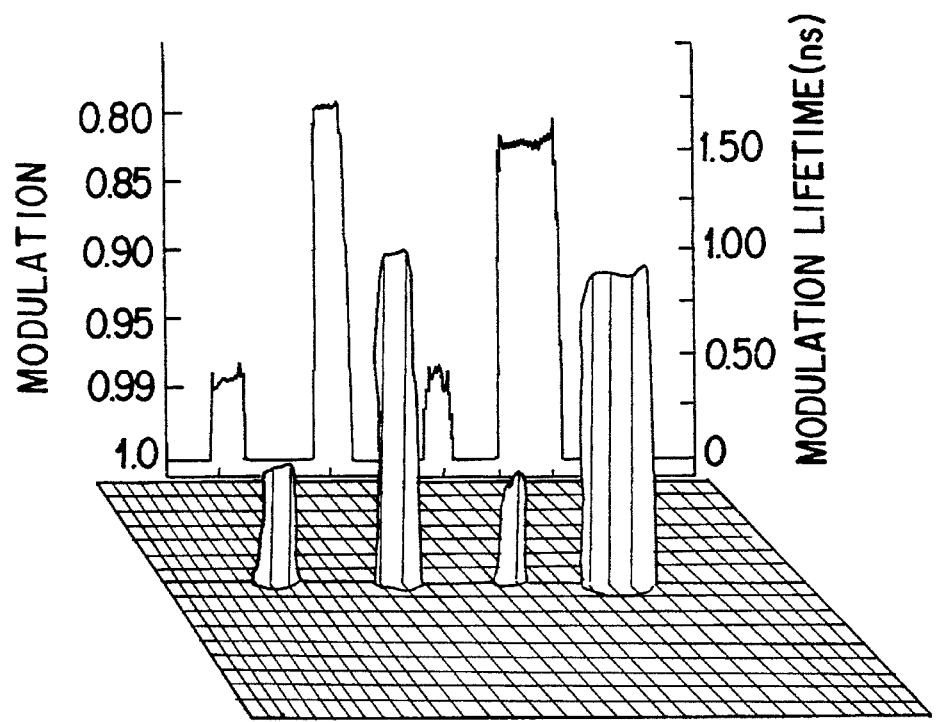

The phase sensitive images, when collected over a range of detector phase angles, allow calculation of the phase angle and modulation at each pixel. Phase and modulation images of the NADH solutions are shown in FIG. 11. The phase angle and lifetime of MDH-bound NADH is larger than that of free NADH seen on either side (FIG. 11(A)). The larger phase angle is due to the longer lifetime of bound NADH. Similarly, the modulation of bound NADH is smaller than that of free NADH (FIG. 11(B)).

Figure 12:
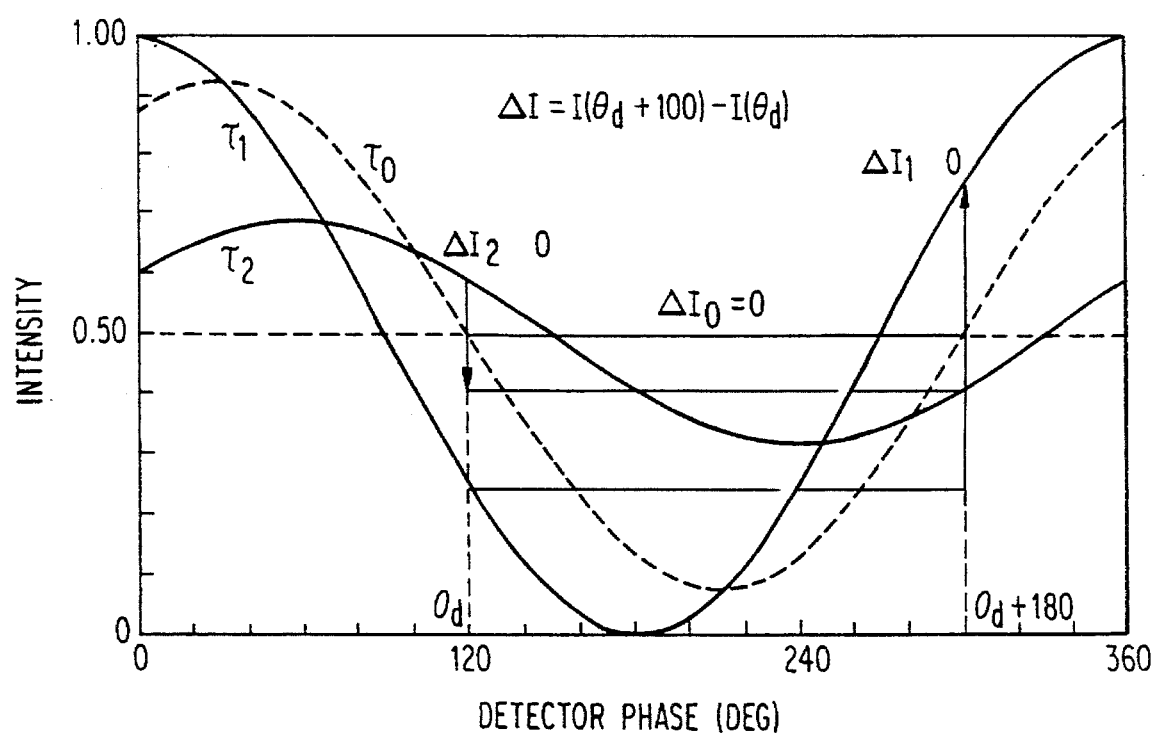
FIG. 12 is a graphical representation of conceptual descriptions of phase suppression.

As described above, a unique property of FLIM is the ability to suppress the emission for any desired lifetime. This concept is shown schematically in FIG. 12. Suppression of any given decay time can be accomplished by taking the difference of two phase sensitive images obtained for detector phase angles of $\Theta_D + 180$ and $\Theta_D$. In the difference image $(I(\Theta_D+180)-I(\Theta_D))$ components with decay time larger than the suppressed lifetime ($\tau_o = \omega^{-1} \tan \Theta_D$) appear as negative regions in the images, and components with shorter lifetimes have positive intensity.

Figure 13A:
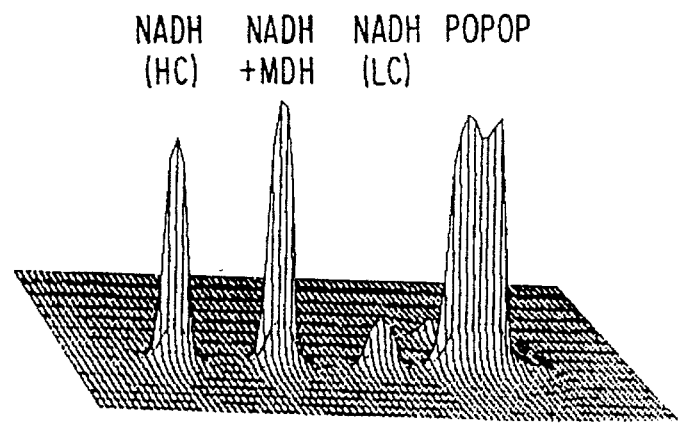
FIG. 13(A)–13(C) are graphical representations of phase-suppressed data images of free and bound NADH and respectively depict: a graphical representation of phase-sensitive data image for $\Theta_D=299.9°$; a graphical representation of difference data image for $I(335.7°) - I(88.1°)$; and a graphical representation of difference data image for $I(129.1°) - I(299.7°)$.
Figure 13B:
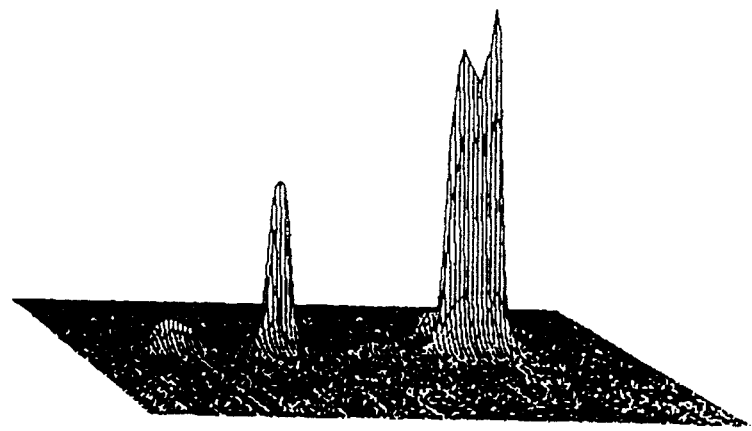
Figure 13C:
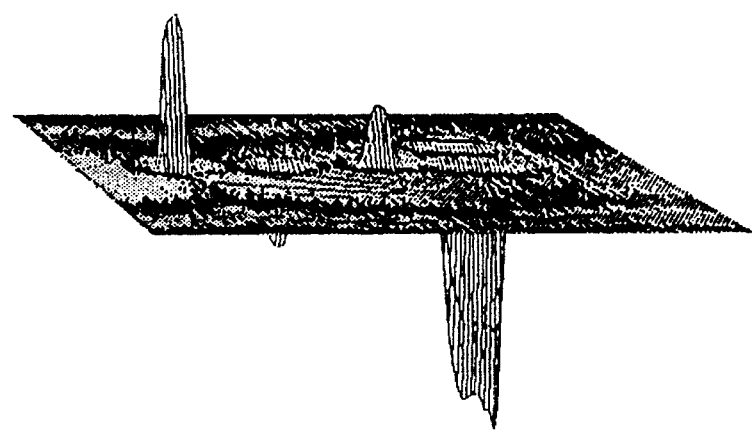

The use of difference images to suppress the emission of exemplified bound or free NADH is shown in FIGS. 13(A)–13(C), which shows the difference contours with positive and negative intensities. Also shown are the grey-scale images in which only the positive region are shown as non-zero. In these grey-scale images the negative region were assigned zero intensity. FIGS. 13(A) shows a non-processed phase sensitive image, in which all samples appear with non-zero intensity. FIG. 13(B) shows where the emission of free NADH is suppressed, revealing a positive peak between the two free NADH samples. Similarly, in FIG. 13(C), the emission of bound NADH is suppressed, revealing two positive images for free NADH on either side of the central sample of bound NADH.

TABLE 3

PHASE MODULATION AND LIFETIME DATA FOR NADH

| SAMPLE | METHOD[a] | PHASE θ(deg) | PHASE $Y_\pi$(ns) | MODULATION m | MODULATION $\tau_m$(ns) |
|---|---|---|---|---|---|
| NADH (HC) | FD | 10.4 | 0.37 | 0.952 | 0.64 |
|  | Cosine | 10.3 | 0.38 ± 0.22 | 1.044 | 0–1.03 |
|  | CCD FT | 10.6 | 0.39 ± 0.02 | 0.985[c] | 0.37 ± 0.36 |
| NADH (LC) | FD | 10.7 | 0.38 | 0.938 | 0.74 |
|  | Cosine | 8.2 | 0.30 ± 0.25 | 1.016 | 0–1.38 |
|  | CCD FT | 8.8 | 0.32 ± 0.02 | 0.872[c] | 0.51 ± 0.24 |
| NADH + MDH | FD | 24.2 | 0.94 | 0.710 | 2.0 |
|  | Cosine | 18.4 | 0.70 ± 0.21 | 0.822 | 1.45 ± 0.50 |
|  | CCD FT | 18.1 | 0.72 ± 0.02 | 0.781[c] | 1.62 ± 0.16 |
| POPOP[b] | FD | 26.6 | 1.05 | 0.885 | 1.10 |
|  |  |  |  | 0.833[c] | 1.39 |

[a] FD indicates standard frequency-domain measurements. Cosine refers to phase and modulation values obtained by least-squares fitting the $\theta_A$-dependent values, as shown in FIG. 10(E). CCD FT references to the pixel-by-pixel analysis.
[b] POPOP in cyclohexame was used as reference sample.
[c] A modulation of 0.833 for POPOP was used as reference modulation for CCD FT calculations (to obtain modulation lifetime for NADH larger than zero)

Figure 23C:
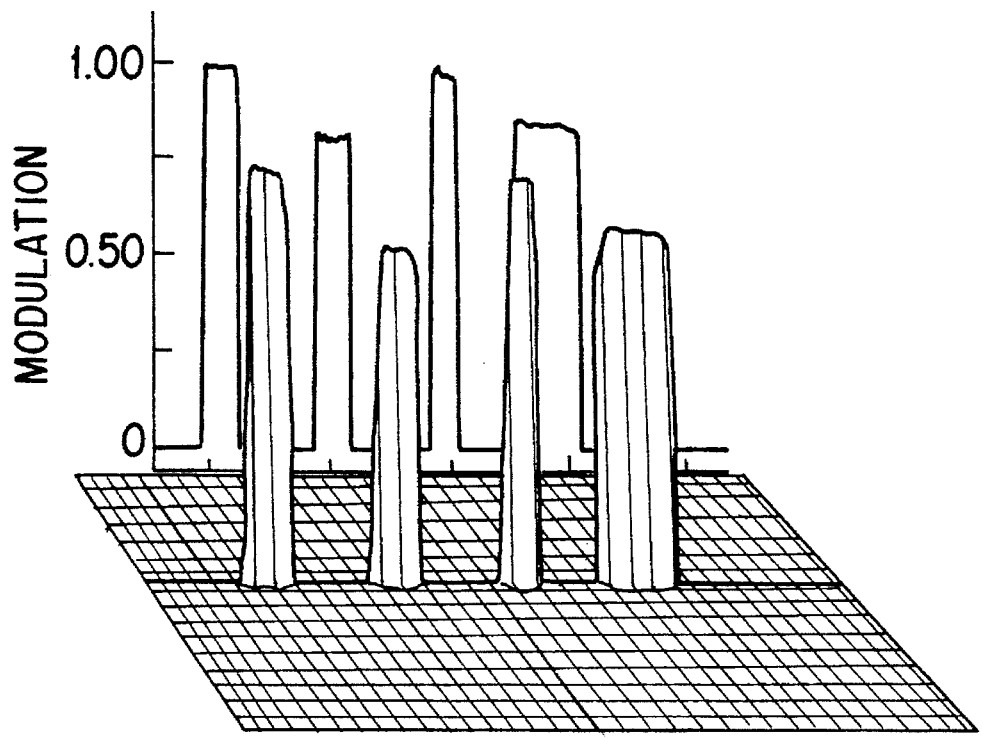
FIG. 23(A) and 23(D) are graphical representations of data images for phase, modulation and lifetime imaging of NADH at $F_{MOD}=75.998$ MHz.
Figure 23D:
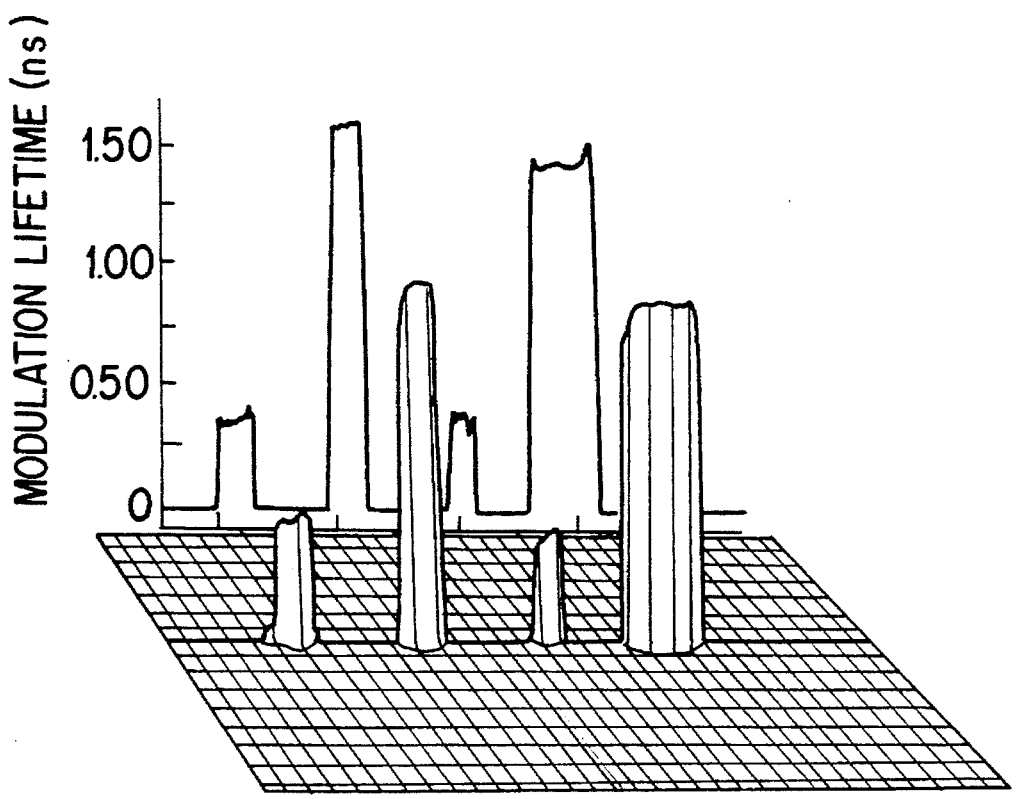

Additionally, FIG. 23 presents 2 dimensional and dimensional graphical representations of phase, modulation and lifetime imaging at a modulation frequency of 75.998 MHz for NADH at varying concentrations using POPOP as a standard.

EXAMPLE 2: FLUORESCENCE LIFETIME IMAGING OF RHODAMINE 6G

Fluorescence lifetime imaging measurements were made for the fluorophore rhodamine 6G according to Example 1 above, with the following parameters. The modulation frequency was 76.2 MHz and potassium iodide was added to the rhodamine 6G as a quencher to provide variable readings, wherein 0.0, 0.03 and 0.1M potassium iodide was added to rhodamine 6G at a concentration of The concentrations of Rhodamine 6G were $3 \times 10^{-6}$M, $5 \times 10^{-6}$M and $1 \times 10^{-5}$M, for iodide concentrations of 0.0, 0.03 and 0.1M, respectively. The concentrations of R6G were varied to keep the intensities approximately equal in all samples.

Figure 18A:
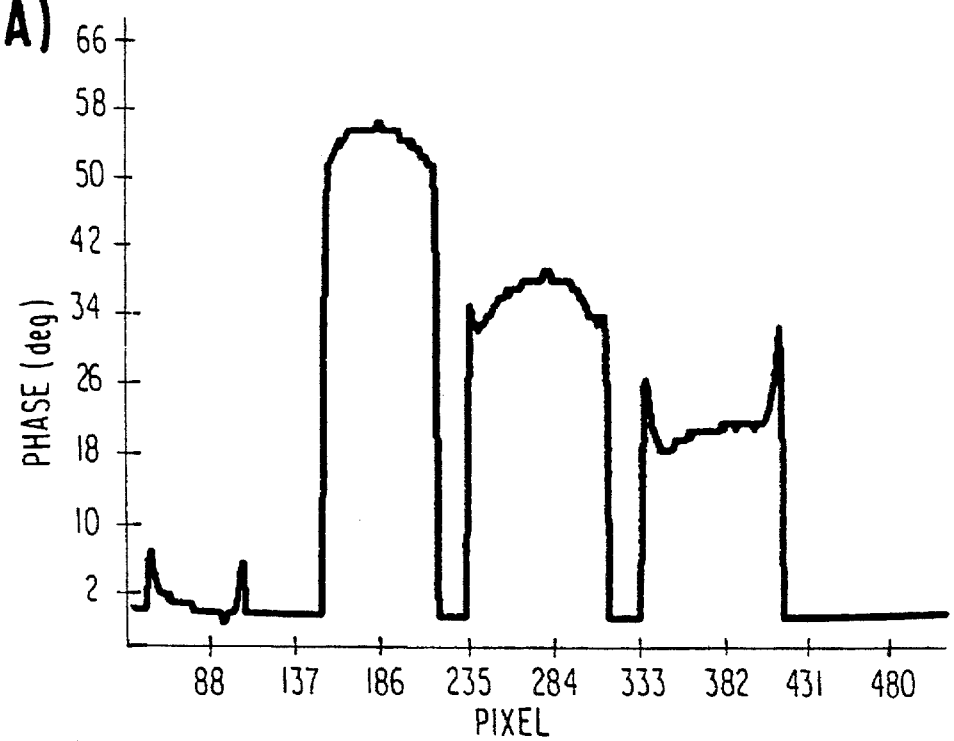
FIG. 18 (A) and 18 (B) are graphical representations of data images for phase and modulation imaging using rhodamine 6G quenched by potassium iodide at $F_{MOD}=76.2$ MHz, for a scatterer, 0, 0.03 and 0.1 M iodide, plotted as per phase angle vs. pixel (FIG. 18(A)) and percent modulation vs. pixel (FIG. 18(B)).
Figure 18B:
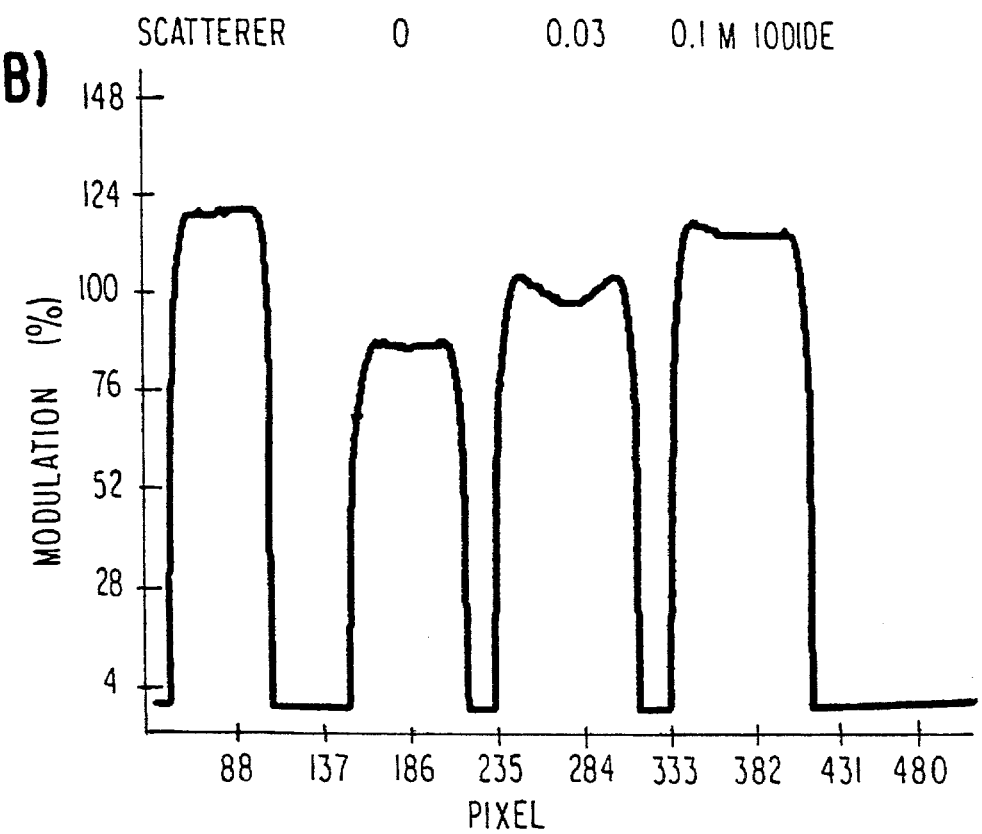
Figure 19A:
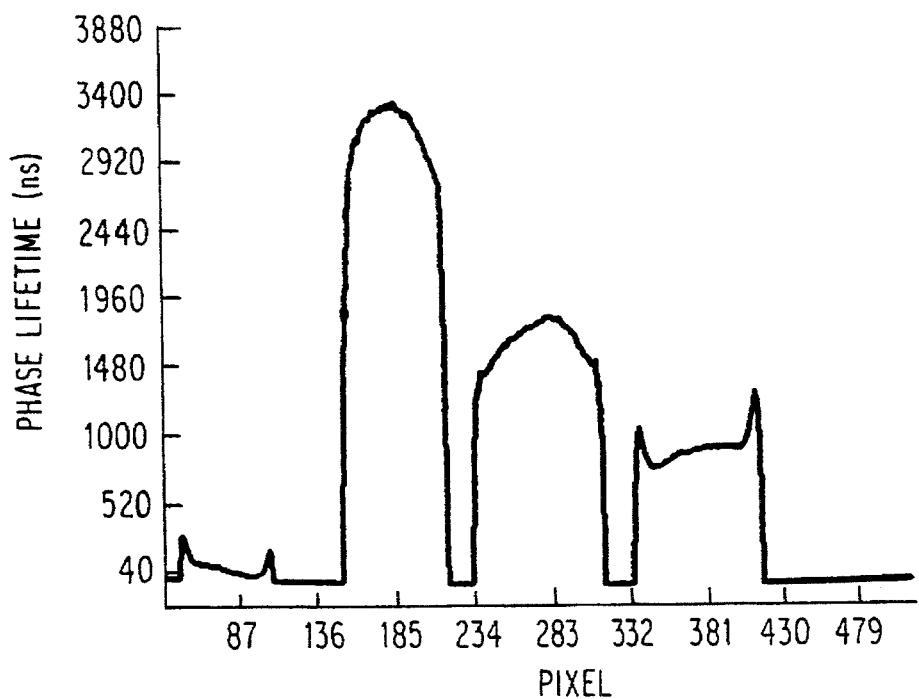
FIG. 19(A) and 19(B) are graphical representations of data images for lifetime imaging of rhodamine 6G quenched by potassium iodide using 0, 0.03 and 0.1 M iodide, wherein phase lifetime (ns) and modulation lifetime (ns), respectively are plotted vs. pixel.
Figure 19B:
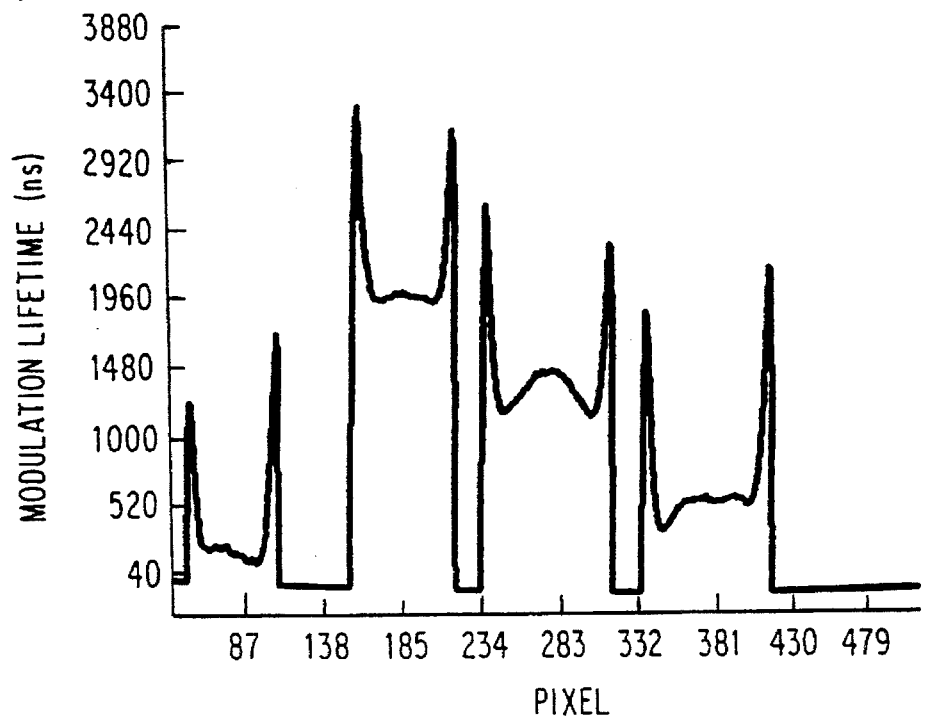

Results. Three solutions, two with iodide added and one without, were placed in three cuvettes and excited with the 568 nm laser beam with the results shown in FIGS. 18(A)–18(B), 19(A)–19(B). Phase sensitive images were collected at a number of detector phase angles (not shown), and were used to construct the phase, modulation and lifetime images shown in 18(A)–19(B) as a 2D image from the illuminated solution with an additional tracing of the intensity measured for a line across the image, plotted as phase in degrees vs. pixel. FIG. 18(B) shows a similar representation as FIG. 18(A), wherein phase in degrees is replaced by percent modulation vs. pixel for the same solutions. Additionally, FIGS. 19(A)–19(B) shows the same solutions as presented above, wherein FIG. 19(A) presents phase lifetime (ns) plotted vs. pixel, and FIG. 19(B) shows modulation of lifetime (ns) vs. pixel.

As expected, the addition of the quencher potassium iodide reduced the phase and modulation lifetimes and the corresponding change in phase angle, as well as increasing percent modulation. Accordingly, the larger phase angle is due to the longer lifetime of the rhodamine 6G with less potassium iodide present.

EXAMPLE 3: FLUORESCENCE LIFETIME IMAGING OF 1,2-BENZANTHRACENE AND/OR OXYGEN

Figure 20A:
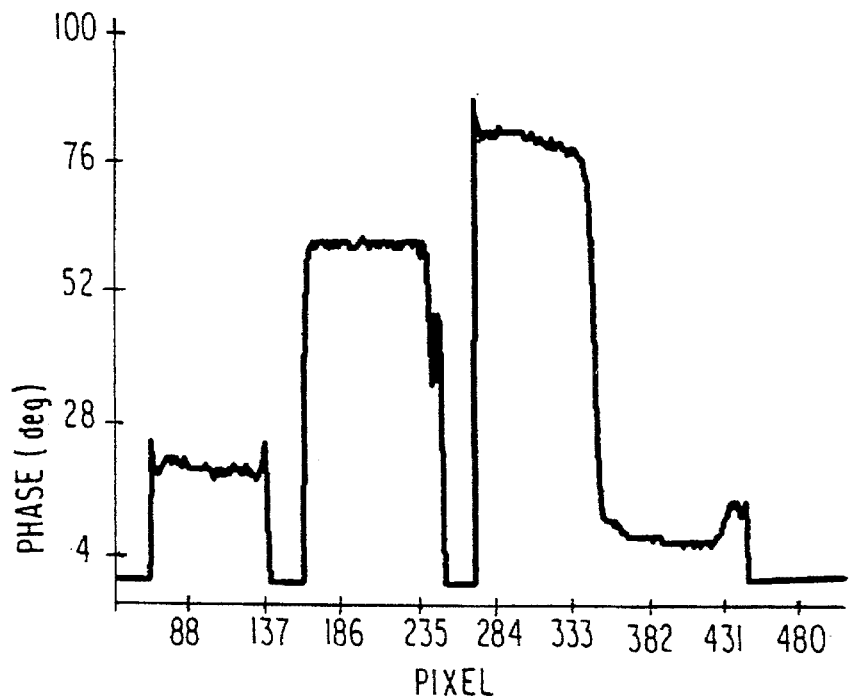
FIG. 20(A) and 20(B) are graphical representations of data images for phase and modulation imaging of 1,2- benzanthracene quenched by oxygen at $F_{MOD}=181.995$ MHz, wherein oxygen, air, air argon and POPOP data are plotted as phase angles (FIG. 20(A)) and percent modulation (FIG. 20(B)) vs. pixel, respectively.
Figure 20B:
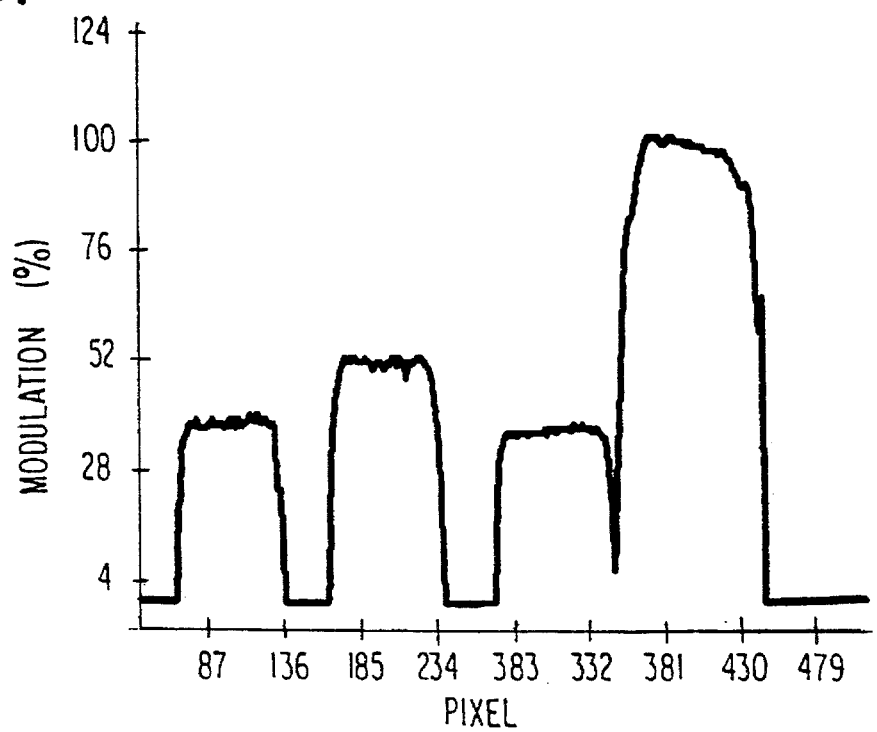

Fluorescence lifetime imaging of 1,2-benzanthracene was carried out according to Example 1 above, wherein modulation frequency was 18.995 MHz, and solutions of pure oxygen, air, and air plus argon were used as sample solutions for phase and modulation imaging. Four solutions, three with 1,2-benzanthracene and one containing POPOP, were placed in four cuvettes and excited with a 355 nm laser beam, as shown schematically in FIG. 8. The phases of images were collected at a number of detector phase angles. Representative images are shown in the FIG. 20(A) change in phase angle (deg) and percent modulation in FIG. 20(B).

As expected, the phase angle increased in proportion to a decrease in oxygen. The modulation with argon (FIG. 20(B)) was in error due to a difficulty which has since been corrected.

Accordingly, the present invention is shown to provide a reliable lifetime imaging of fluorophores which directly respond to environmental changes adjacent to the fluorophore.

EXAMPLE 4: FLUORESCENCE LIFETIME IMAGING OF CALCIUM USING QUIN-2

Calcium lifetime imaging was performed according to the methods of additional Example 1 above, wherein the modulation frequency was 49.53 MHz, using the fluorophore Quin-2 at calcium concentrations of 0, 26 and 211 micromolar.

Figure 21:
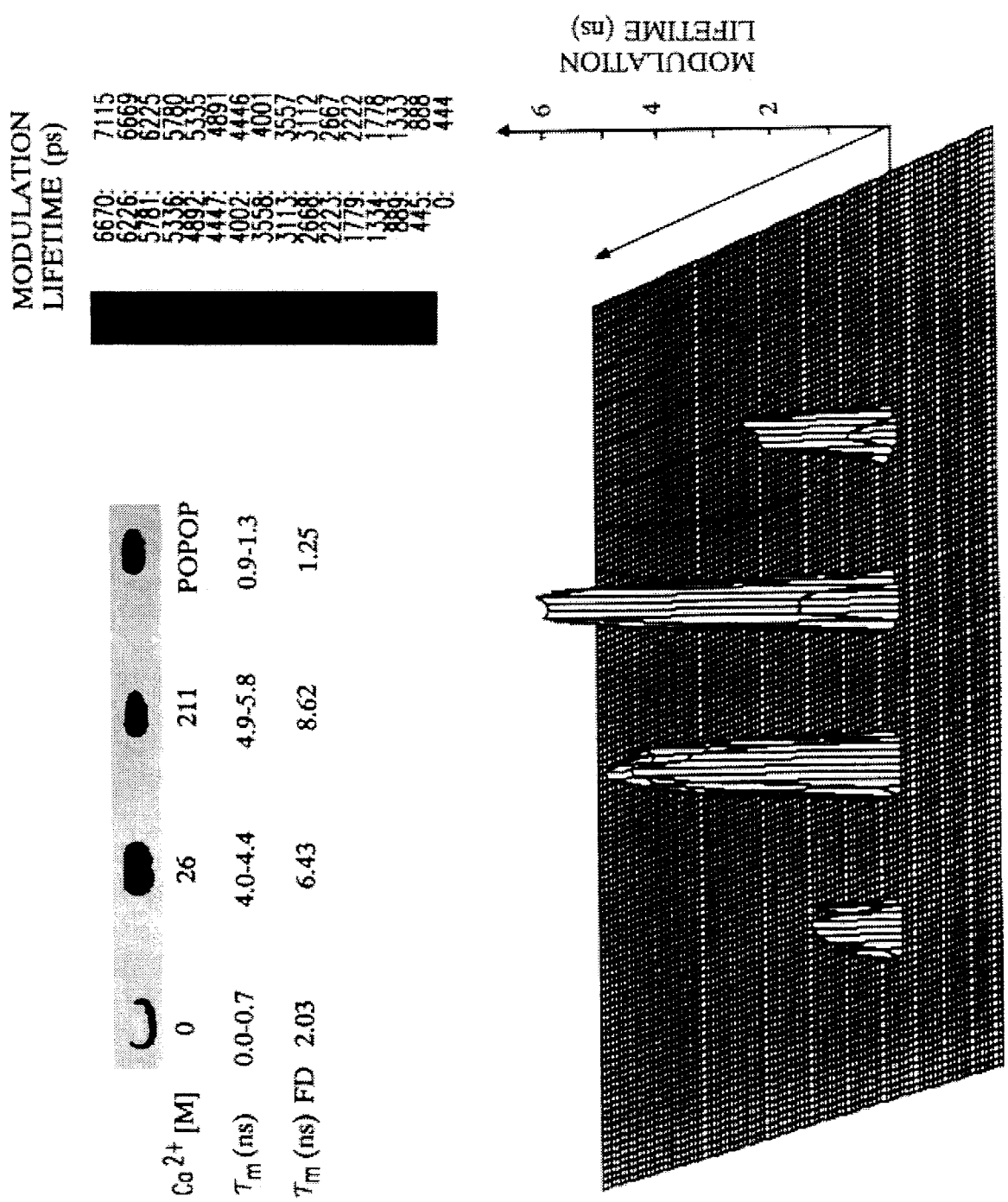
FIG. 21 is a 3D graphical representation of data images for calcium imaging by the fluorophore Quin-2, using modulation of lifetimes at $F_{MOD}=49.53$ MHz, wherein modulation lifetime (ns) is plotted vs. pixel for varying concentrations of $Ca^{2+}$.
Figure 22:
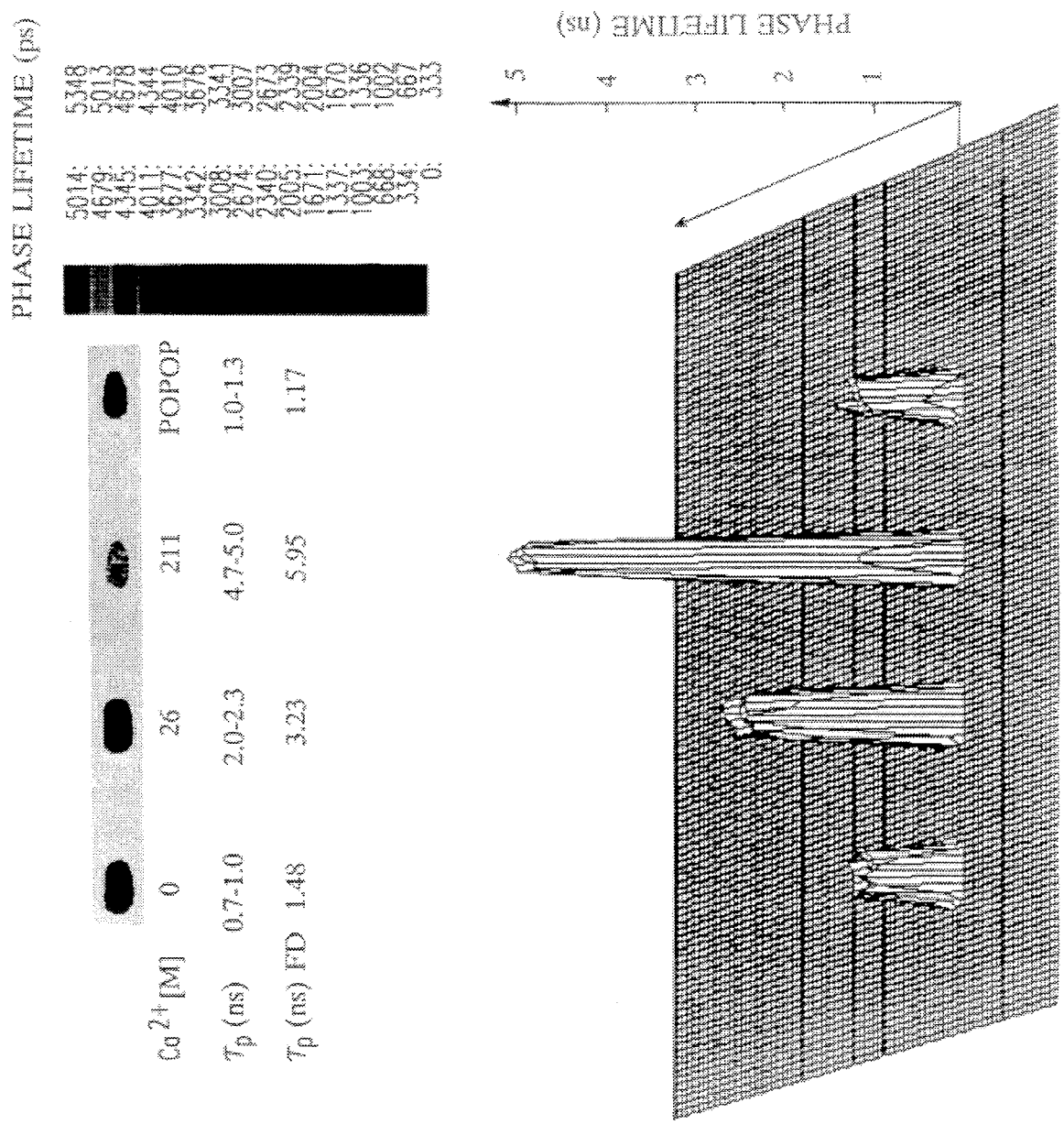
FIG. 22 is a 3D graphical representation of data images, as presented in FIG. 21, wherein the phase lifetime (ns) is plotted vs. pixel for varying concentrations of $Ca^{2+}$.

Accordingly, sample solutions, one with Quin-2 and no calcium, two with Quin-2 and calcium and one containing POPOP (no Quin-2 or calcium), were placed in four cuvettes and excited with 355 nm laser light, as shown in FIG. 8. The phase-sensitive images were collected at a number of detector phase angles. Representative images are shown in FIGS. 21 and 22, which show 3D images from the illuminated solutions, for modulation lifetime (ps) and phase lifetime (ps), respectively, wherein phase and modulation lifetime are plotted above the horizontal relative to the pixel.

Lifetimes for the fluorophore Quin-2 were proportionally and reproducibly modified by the presence of calcium, wherein the lifetime was appreciable increased.

Quin-2 is used less often for $Ca^{++}$ imaging than Fura-2 because Quin-2 is not useful in a wavelength ratiometric probe used in known fluorescence measurements using intensity wavelength ratios. Accordingly, the the present invention provides for $Ca^{++}$ measurements with non-ratiometric probes which are more available and which can have longer excitation and emission wavelengths.

Therefore, the present method provides a means to image varying concentrations of physically distinguishable characteristics as analytes over a relatively wide area, which correpond to micro-environmental changes in, e.g., analyte concentrations.

It should be understood, however, that the above description and specific examples, while indicating preferred embodiments of the present invention, are given by way of illustration and not limitation.

Many changes and modifications within the scope of the present invention may be made without departing from the spirit thereof, and the present invention includes all such modifications.

What is claimed is:

1. A method for performing multi-dimensional optical measurements on a subject in a sample containing at least one fluorescent probe, comprising the following steps:

(a) illuminating said fluorescent probe with intensity modulated light at a first wavelength of said probe, said light being intensity modulated at a first frequency and a first phase, to produce secondary light as an excitation emission from said probe, said secondary light being intensity modulated at the first frequency and having a second phase;

(b) generating a gating signal modulated at said first frequency and having a third phase, differing by a first detector phase angle from said first phase;

(c) receiving said secondary light and intensifying said secondary light in response to said gating signal;

(d) generating at least a two dimensional image in response to said intensified secondary light; and (e) detecting said at least two dimensional image;

(f) repeating, at least once, steps (b), (c), (d) and (e) with a second detector phase angle to produce at least two detected images each of which corresponds to a change between the phase and/or modulation of said secondary light and said intensity modulated light; and (g) arithmetically processing the detected images to produce a final lifetime image, wherein said final lifetime image is (a) indicative of a value of the fluorescence lifetime of said at least one fluorescent probe and (b) is independent of the amplitude of the emission signal;

wherein said generating step (d) comprises:

(a) generating a first stored picture by setting said detector phase angle to $\pi/2$ relative to said first phase, detecting said resultant image and storing said detected image as a first picture;

(b) generating a second stored picture without modulation on said grating signal, detecting said resultant image and storing said detected image as a second picture;

(c) generating a third stored picture by setting said detector phase angle to 0° relative to said first phase, detecting said resultant image and storing said detected image as a third picture;

(d) subtracting said second stored picture from said first stored picture to generate a first intermediate image;

(e) subtracting said second stored picture from said third stored picture to generate a second intermediate image; and (f) generating the ratio of said first intermediate image and said second intermediate image, said ratio identifying a pixel intensity that is proportional to said first physical property with respect to said second physical property.

2. The method of claim 1 further comprising using said ratio to discriminate said first physical property from said second physical property.

* * * * *

UNITED STATES PATENT AND TRADEMARK OFFICE
CERTIFICATE OF CORRECTION

PATENT NO.  : 5,485,530
DATED       : January 16, 1996
INVENTOR(S) : Joseph R. Lakowicz et al.

It is certified that error appears in the above-indentified patent and that said Letters Patent is hereby corrected as shown below:

Col. 11, Table 1, under the column subheaded "Dye Type", the fourth line, "Withramycin" should be -- Mithramycin --; Col. 12, Table 2, under the column subheaded "Probe", the first line, "SMARF-1, etc." should be -- SNARF-1, etc. --; Col. 14, line 23, "$f_1 1$," should be -- $f_1$, --; Col. 14, delete line 64 in its entirety, and replace it with -- region with lifetime different from $\tau_1$ --; Col. 18, line 67, "processes,." should be -- processes, --; Col. 20, line 26, "21:6178" should be -- 21:61-78 --; Col. 22, line 3, "FIGS." should be -- FIG. --; Col. 22, line 35, after "and" insert -- 3 --; Col. 24, line 47 (claim 1), "grating" should be -- gating --.

Signed and Sealed this

Second Day of July, 1996

Attest:

BRUCE LEHMAN

*Attesting Officer*    Commissioner of Patents and Trademarks